United States Patent
Sternick

(10) Patent No.: US 9,494,510 B2
(45) Date of Patent: Nov. 15, 2016

(54) CUVETTE SYSTEM

(71) Applicant: John L. Sternick, Brandon, SD (US)

(72) Inventor: John L. Sternick, Brandon, SD (US)

( * ) Notice: Subject to any disclaimer, the term of this patent is extended or adjusted under 35 U.S.C. 154(b) by 0 days.

(21) Appl. No.: 15/016,837

(22) Filed: Feb. 5, 2016

(65) Prior Publication Data

US 2016/0231227 A1    Aug. 11, 2016

Related U.S. Application Data

(63) Continuation-in-part of application No. 14/615,544, filed on Feb. 6, 2015, now Pat. No. 9,279,761.

(51) Int. Cl.
*G01N 21/03* (2006.01)

(52) U.S. Cl.
CPC ... *G01N 21/0303* (2013.01); *G01N 2021/0307* (2013.01); *G01N 2021/0321* (2013.01); *G01N 2201/068* (2013.01)

(58) Field of Classification Search
CPC ............ G01N 21/0303; G01N 2201/02; G01N 21/03; G01N 2021/0375; G01N 2021/0321; G01N 2021/0307
USPC ......... 356/244, 246; 250/576; 422/102, 104, 422/82.09, 547, 561, 562
See application file for complete search history.

(56) References Cited

U.S. PATENT DOCUMENTS

| | | |
|---|---|---|
| 3,556,731 A | 1/1971 | Martin |
| 4,318,994 A | 3/1982 | Meyer |
| 4,332,471 A | 6/1982 | Gross |
| 4,806,316 A | 2/1989 | Johnson |
| 4,999,285 A | 3/1991 | Stiso |
| 5,128,104 A | 7/1992 | Murphy |
| 5,437,841 A * | 8/1995 | Balmer ............... B01L 3/02 356/246 |
| D395,708 S | 6/1998 | Shartle |
| 5,916,525 A | 6/1999 | Husar |
| 6,249,345 B1 | 6/2001 | Kraack |
| 6,589,790 B1 | 7/2003 | Colin |
| 6,929,158 B2 | 8/2005 | Smiley |
| 7,491,546 B2 * | 2/2009 | Jaunakais ......... G01N 31/224 356/436 |
| 7,611,672 B1 * | 11/2009 | Fukunaga ........... G01N 21/03 356/244 |

(Continued)

FOREIGN PATENT DOCUMENTS

WO          0075632       12/2000

*Primary Examiner* — Sang Nguyen
(74) *Attorney, Agent, or Firm* — Jeffrey A. Proehl; Woods, Fuller, Shultz & Smith, P.C

(57) ABSTRACT

A cuvette system may comprise a disposable cuvette element for holding a sample for analysis, with the cuvette element comprising an elongated strip having opposite faces and a well for receiving the sample to be analyzed. The well may be formed on the strip to hold a sample on the strip, and a hole may form at least a portion of the well and may extend through the strip. The well may be configured to hold a defined volume of the sample to be held therein. The system may comprise a reusable holder for removably receiving the cuvette element, with the holder having a substantially hollow interior for receiving at least a portion of the cuvette element. The holder may have a perimeter wall including a front wall and a rear wall of the holder, and a window may be formed in each of the front and rear walls and may be generally positioned in alignment with each other. The windows may be alignable with the well in the cuvette element when the cuvette element is inserted into the holder such that a straight line passes through the windows and the well simultaneously.

19 Claims, 23 Drawing Sheets

(56) References Cited

U.S. PATENT DOCUMENTS

| | | | |
|---|---|---|---|
| 8,512,279 B2 * | 8/2013 | Klein | G01N 21/11 604/93.01 |
| 8,537,352 B2 | 9/2013 | Eikelmann | |
| 8,802,029 B2 | 8/2014 | Steinmiller | |
| 2005/0013746 A1 * | 1/2005 | Lee | B01L 3/508 422/547 |
| 2007/0019189 A1 | 1/2007 | Marsteller | |
| 2010/0104475 A1 | 4/2010 | Miyoshi | |
| 2011/0164245 A1 | 7/2011 | Eikelmann | |
| 2011/0170094 A1 | 7/2011 | Harnack | |
| 2012/0322052 A1 | 12/2012 | Halverson | |

* cited by examiner

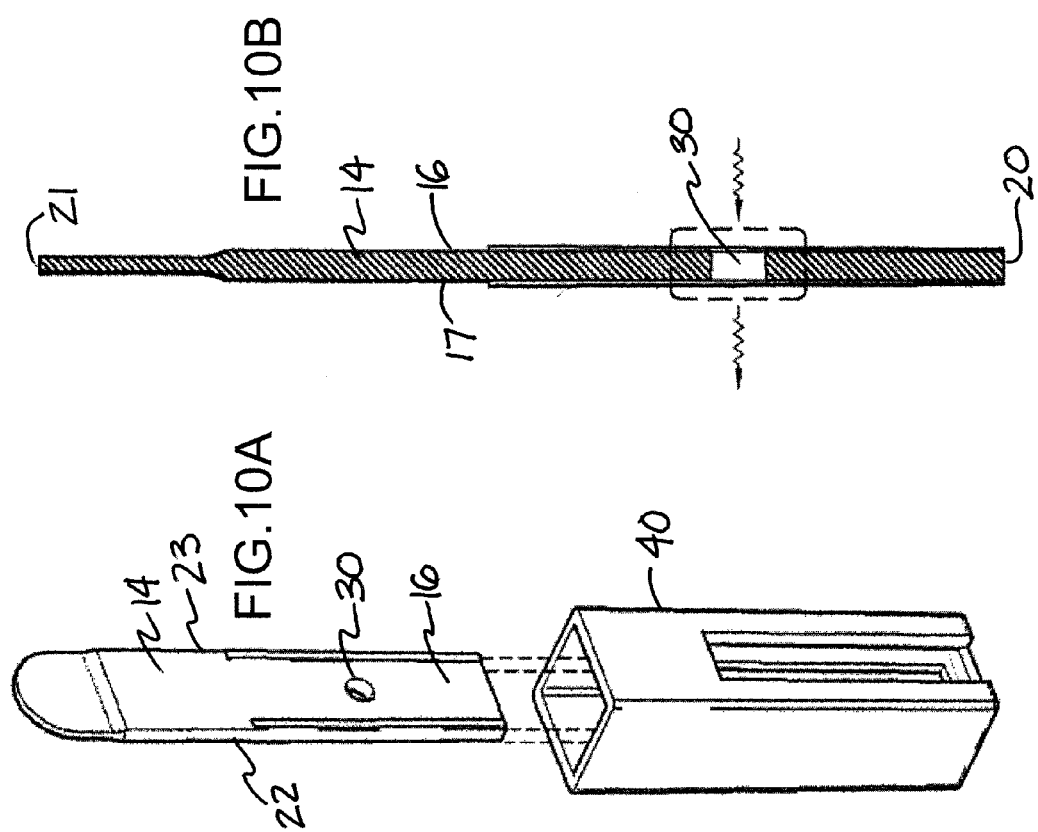

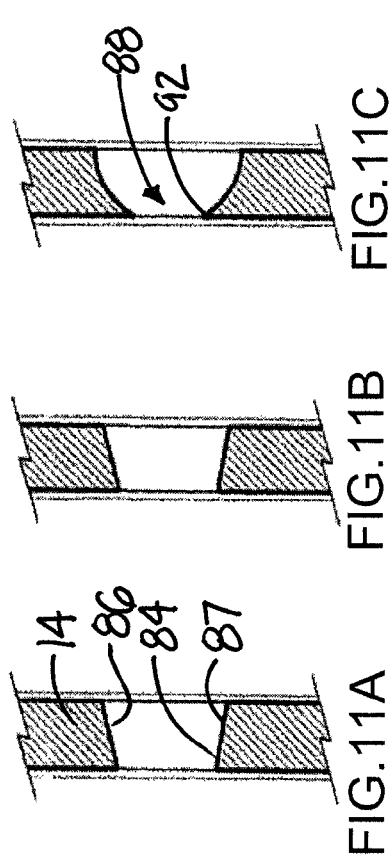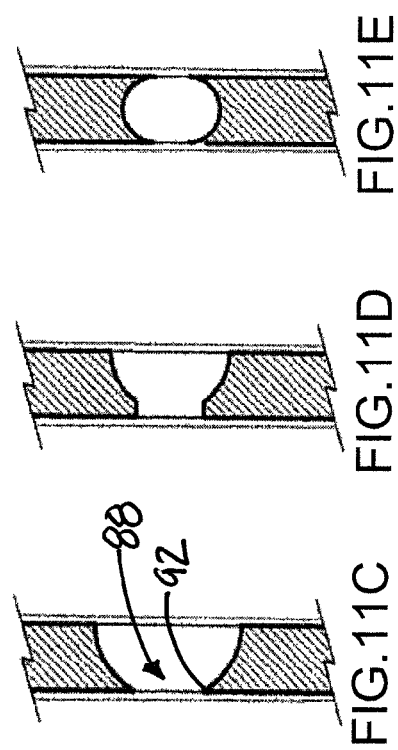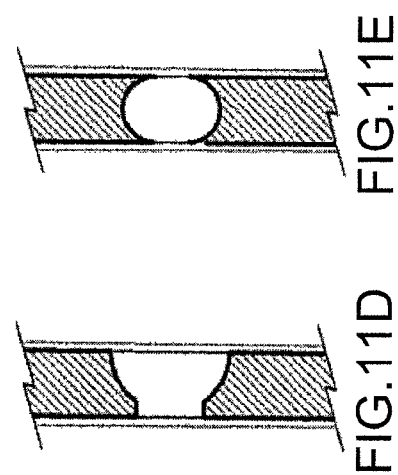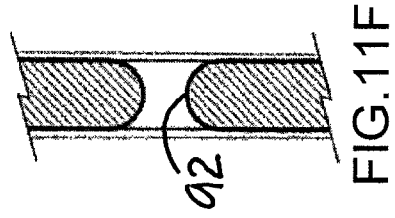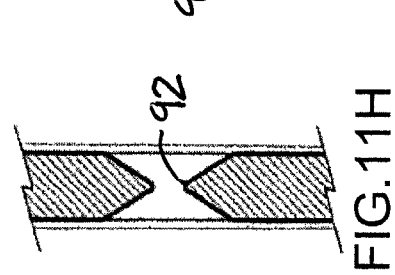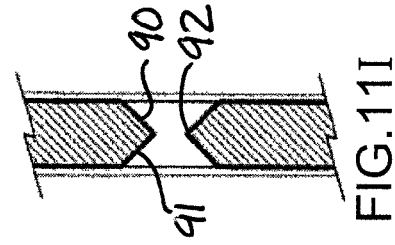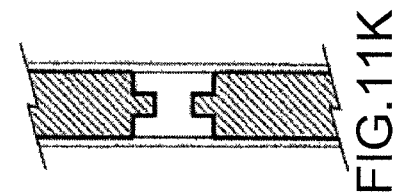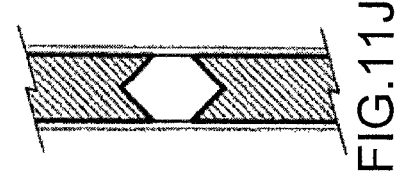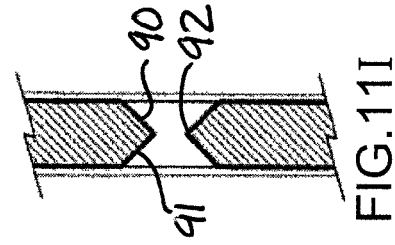

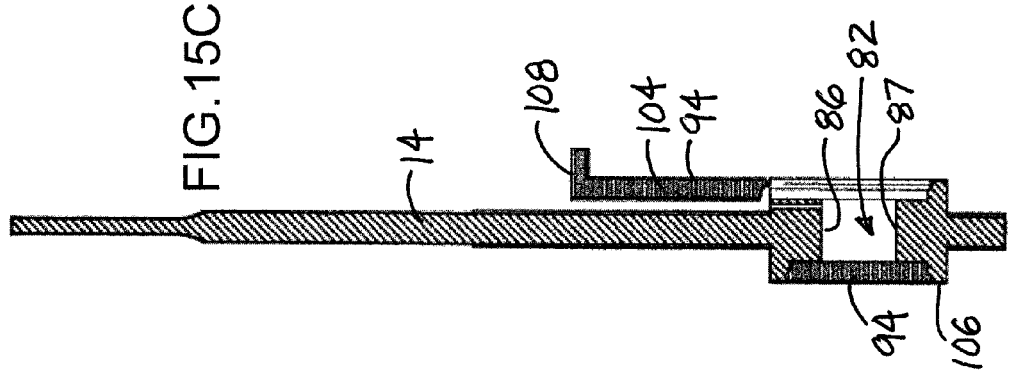
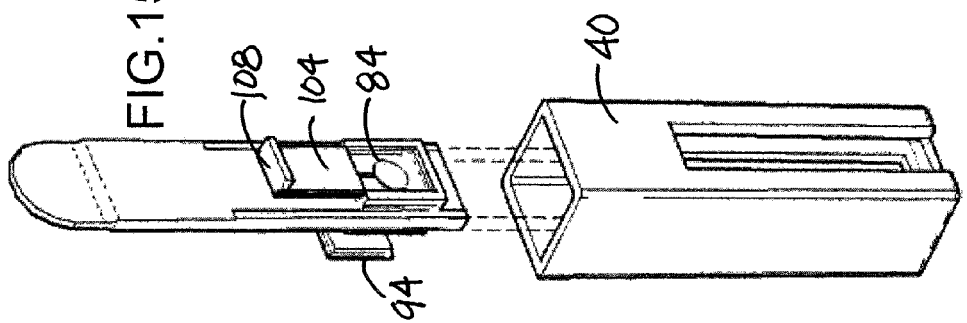
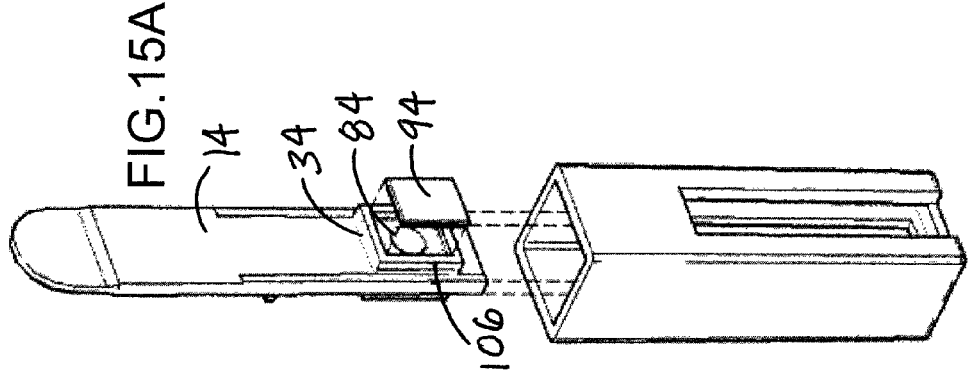

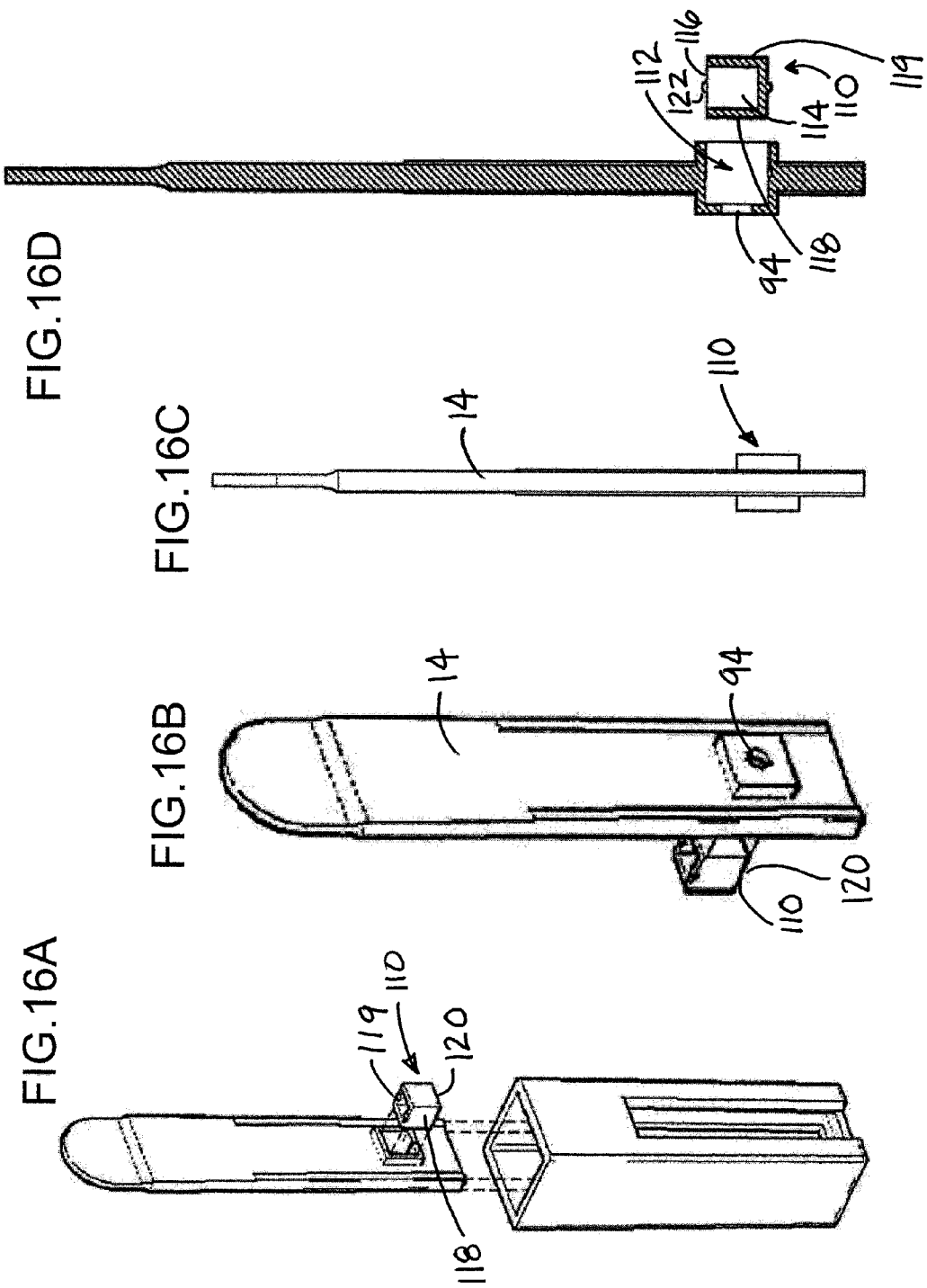

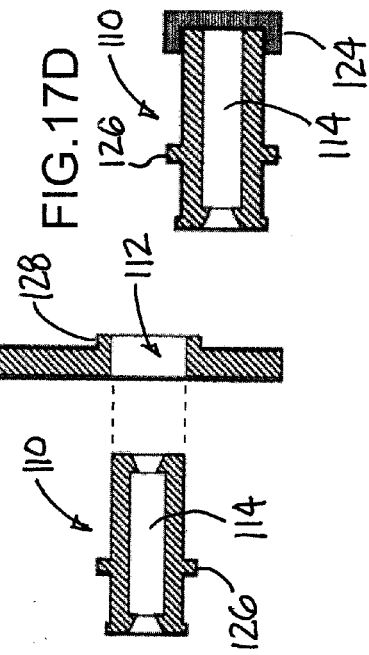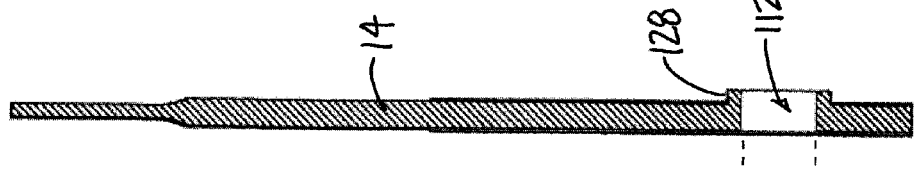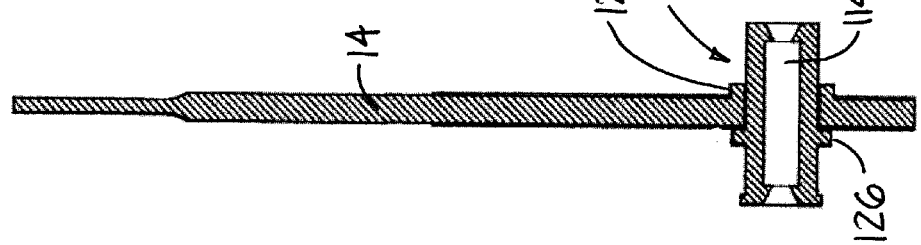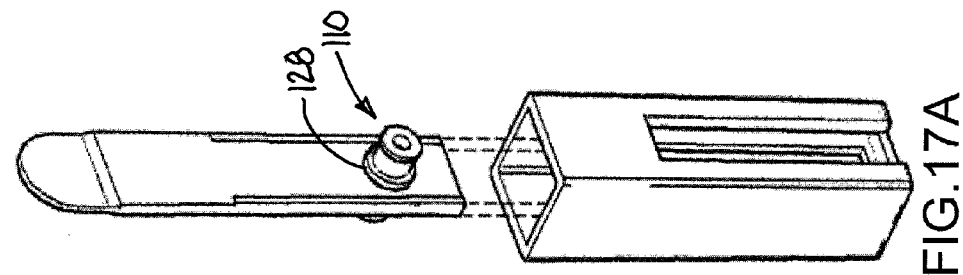

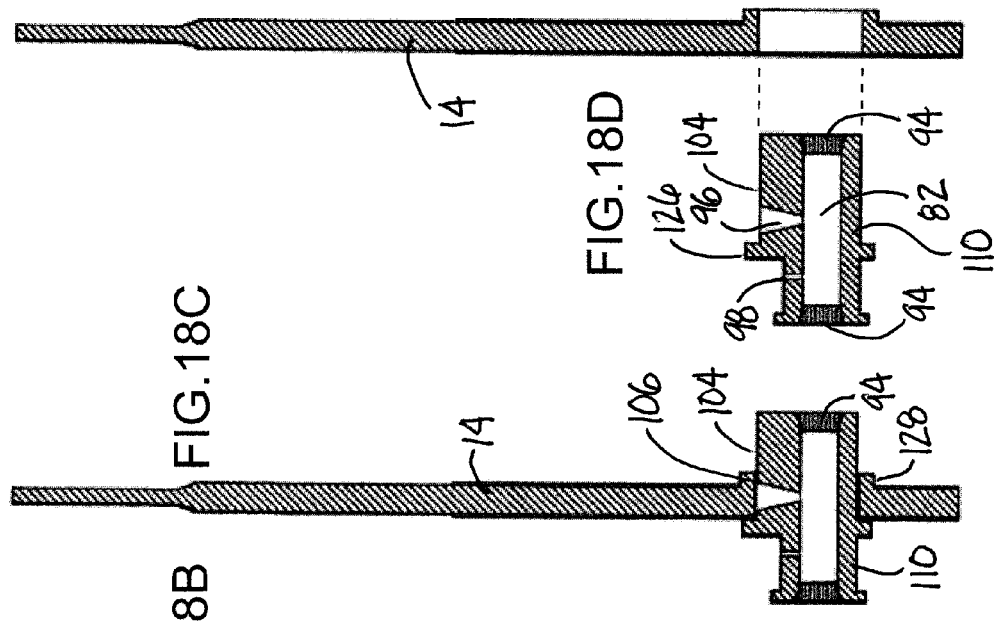

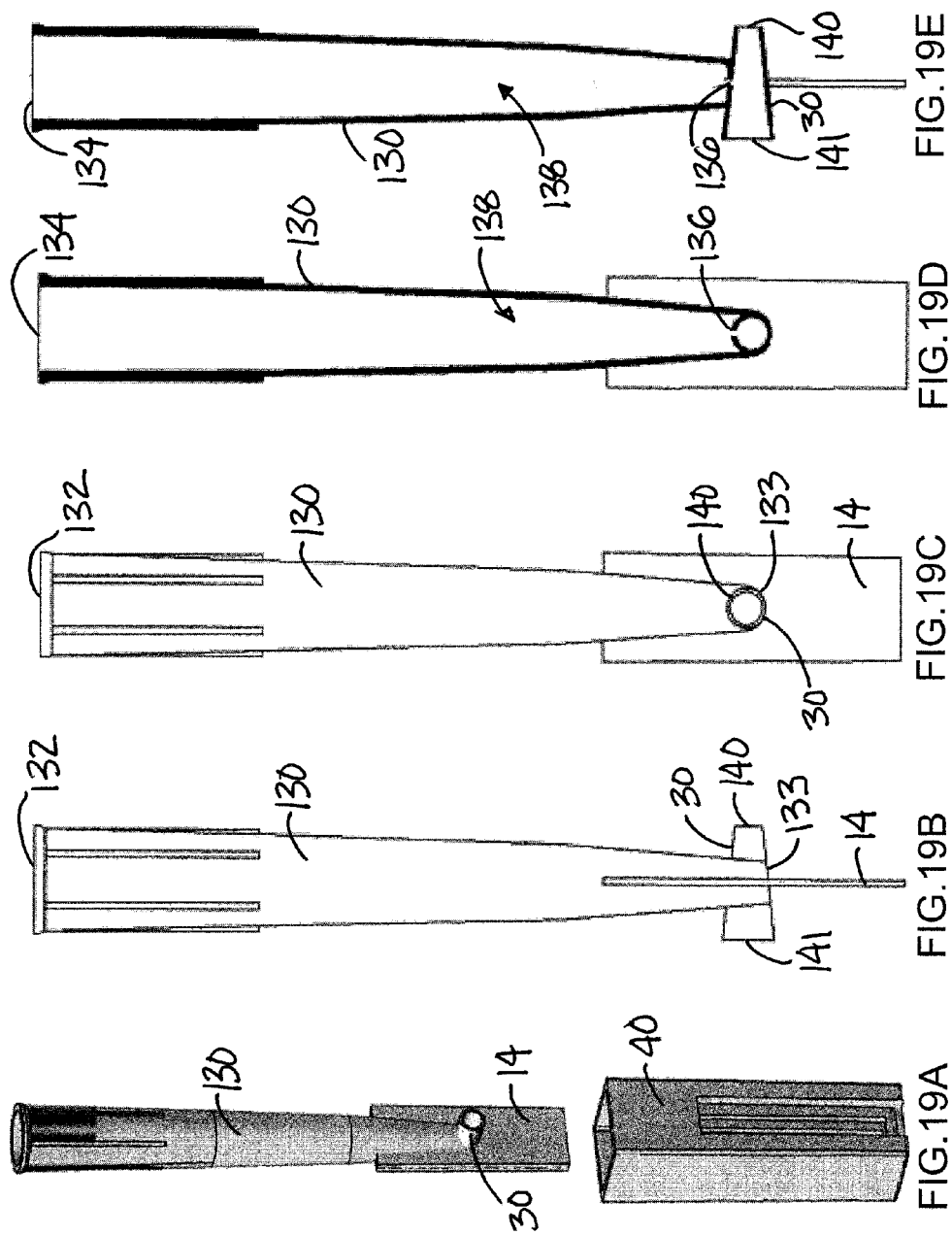

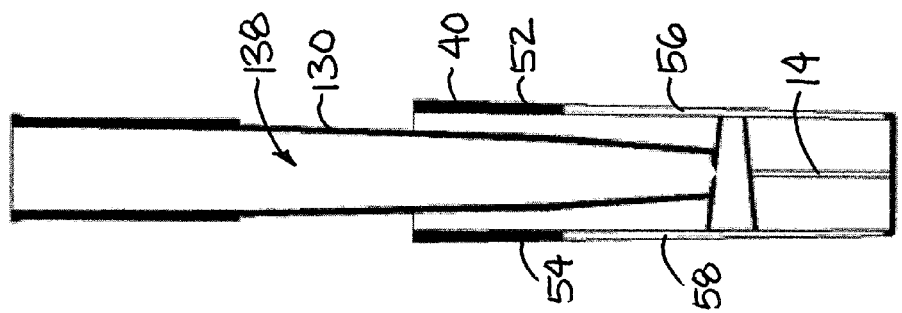
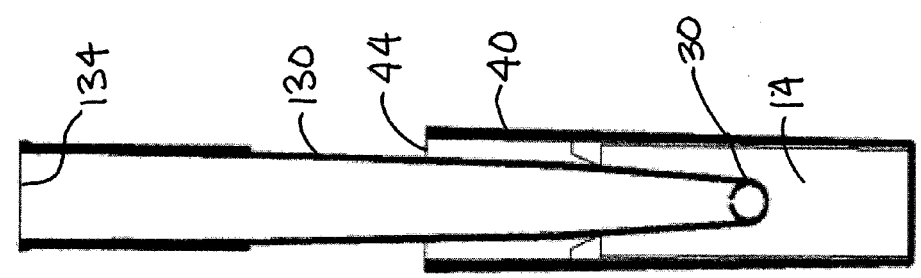
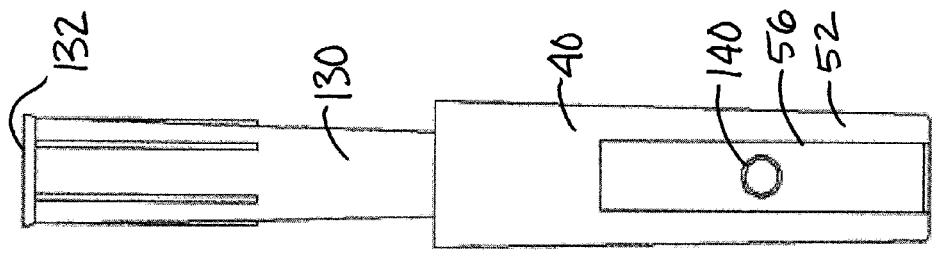

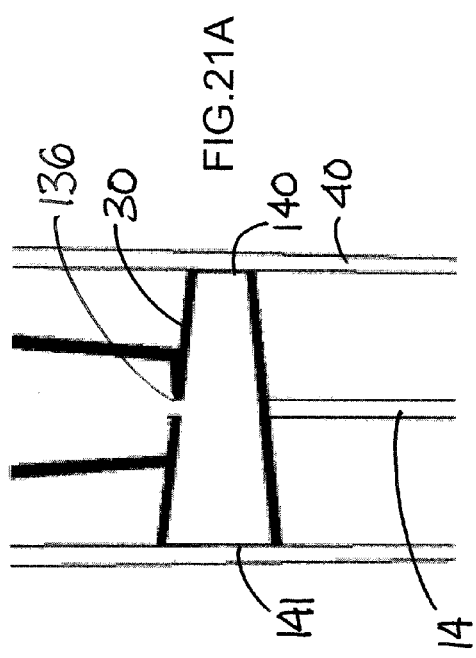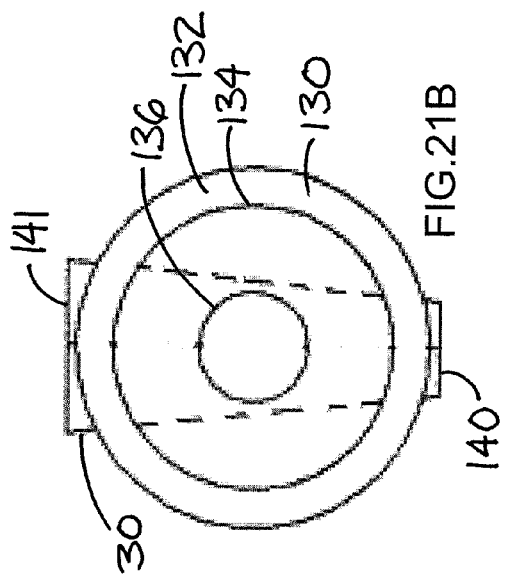

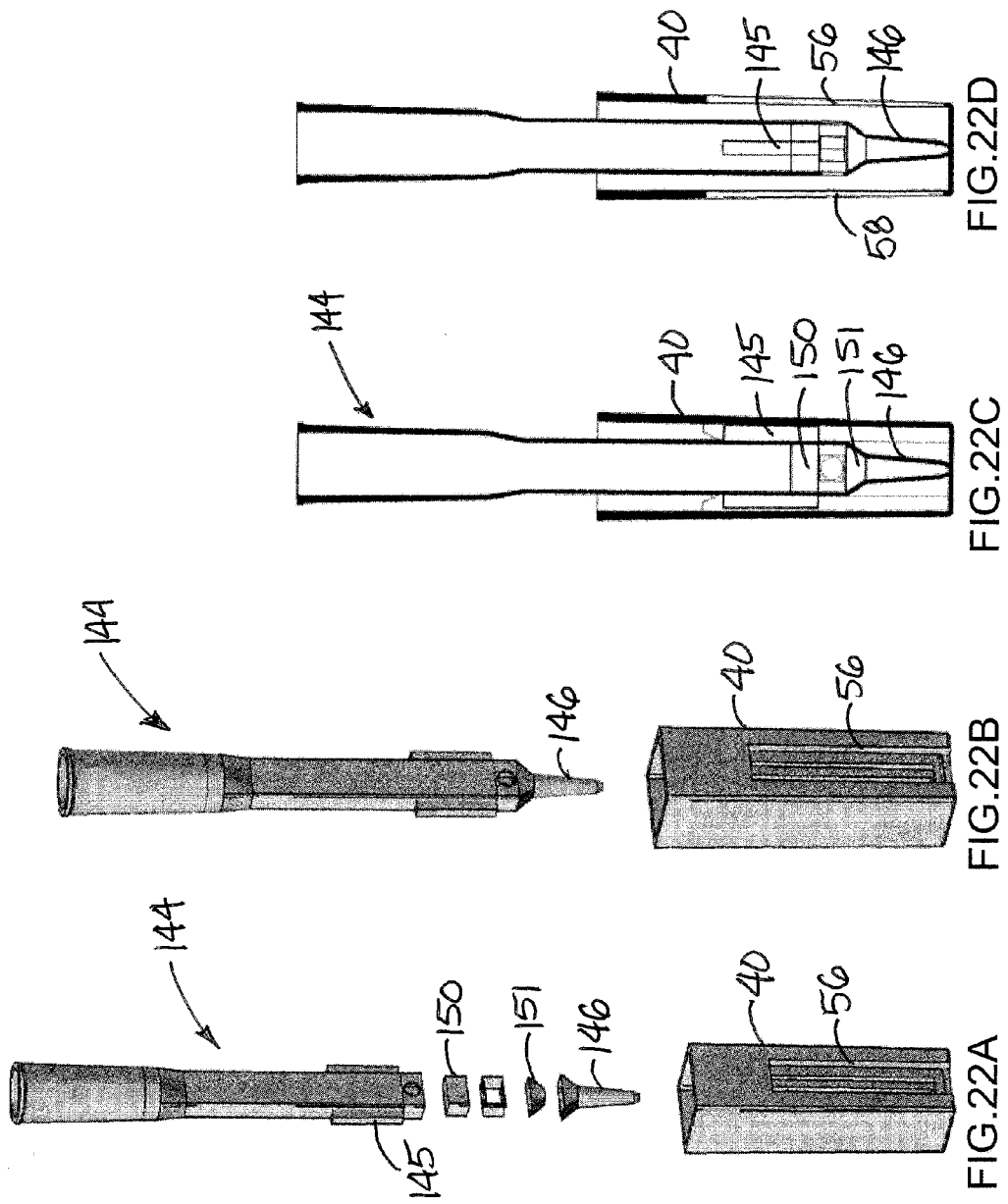

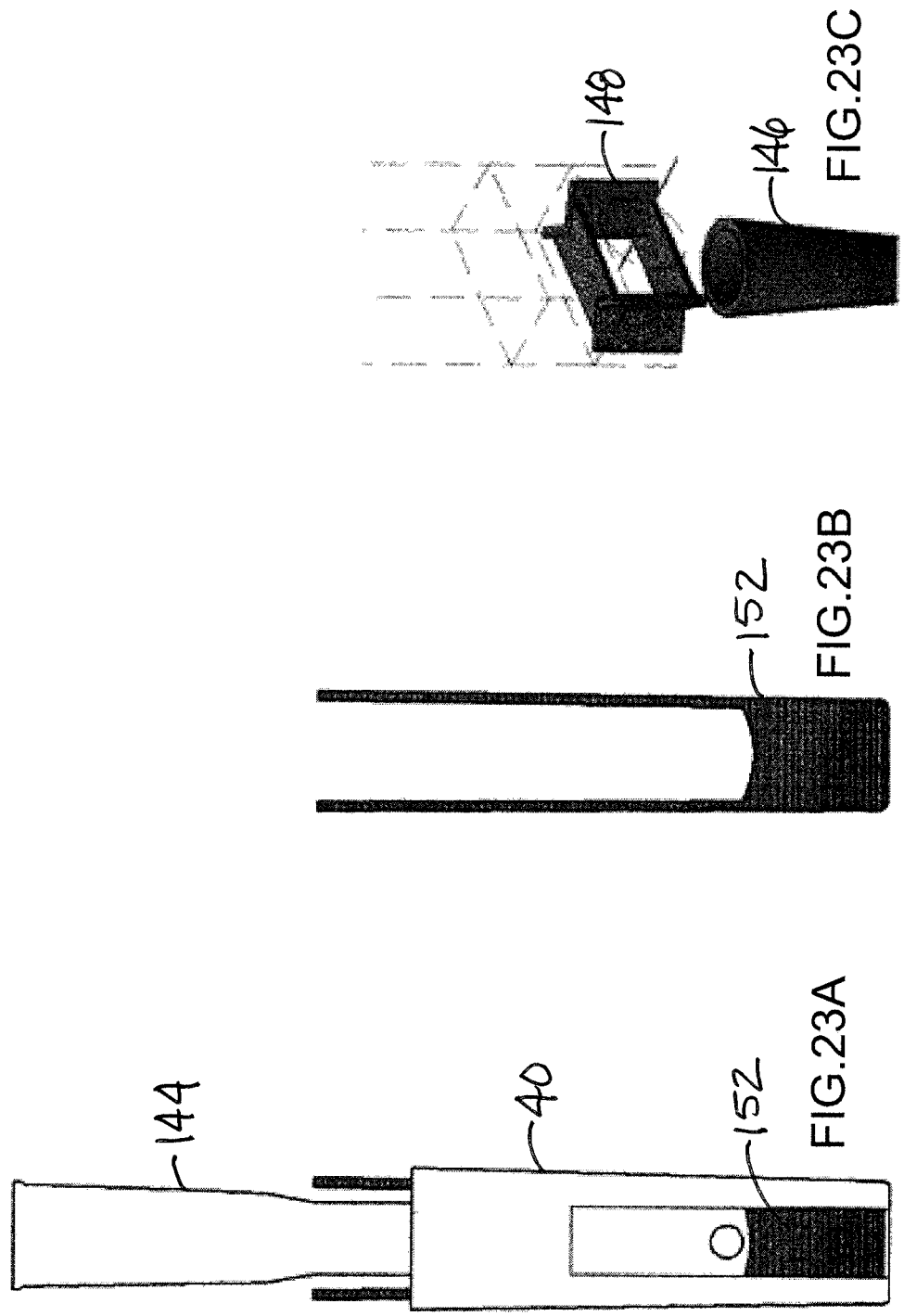

CUVETTE SYSTEM

REFERENCE TO RELATED APPLICATION

This application is a continuation-in-part of U.S. patent application Ser. No. 14/615,544, filed Feb. 6, 2015, wherein is hereby incorporated by reference in its entirety.

BACKGROUND

Field

The present disclosure relates to cuvettes and more particularly pertains to a new cuvette system that may provide more economical and more accurate testing of samples.

SUMMARY

The present disclosure relates to a cuvette system which may comprise a disposable cuvette element for holding a sample for analysis. The cuvette element may comprise an elongated strip having opposite faces and a well for receiving the sample to be analyzed. The well may be formed on the strip to hold a sample on the strip, and a hole may form at least a portion of the well and may extend through the strip. The well may be configured to hold a defined volume of the sample to be held therein. The system may comprise a reusable holder for removably receiving the cuvette element, with the holder having a substantially hollow interior for receiving at least a portion of the cuvette element. The holder may have a perimeter wall including a front wall and a rear wall of the holder, and a window may be formed in each of the front and rear walls and may be generally positioned in alignment with each other. The windows may be alignable with the well in the cuvette element when the cuvette element is inserted into the holder such that a straight line passes through the windows and the well simultaneously.

In another aspect, the disclosure relates to a cuvette system that may comprise a disposable cuvette element for holding a sample for analysis. The cuvette element may comprise an elongated strip having an exterior surface with opposite faces, and a well formed on the strip to hold a sample on the strip. The well may define a closed space forming a reservoir configured to hold a defined volume of the sample to be held in the strip, and at least one passage may be formed in the strip. The passage may be in fluid communication with the reservoir and with an opening in the exterior surface of the strip. The cuvette system may also comprise a reusable holder for removably receiving the cuvette element, which may have a substantially hollow interior for receiving at least a portion of the cuvette element. The holder may have a perimeter wall including a front wall and a rear wall of the holder, and a window may be formed in each of the front and rear walls and being generally positioned in alignment with each other. The windows may be alignable with the well in the cuvette element when the cuvette element is inserted into the holder such that a straight line passes through the windows and the well simultaneously.

In still another aspect, the disclosure relates to a cuvette system that may comprise a disposable cuvette element for holding a sample for analysis. The cuvette element may comprise an elongated strip having an exterior surface with opposite faces, and a well formed on the strip to hold a sample on the strip. The well may define a closed space forming a reservoir configured to hold a defined volume of the sample to be held in the strip. The cuvette system may also comprise a reusable holder for removably receiving the cuvette element, which may have a substantially hollow interior for receiving at least a portion of the cuvette element. The holder may have a perimeter wall including a front wall and a rear wall of the holder, and a window may be formed in each of the front and rear walls and being generally positioned in alignment with each other. The windows may be alignable with the well in the cuvette element when the cuvette element is inserted into the holder such that a straight line passes through the windows and the well simultaneously. The well of the strip may include a movable portion and a remaining portion, with the movable portion being movable with respect to a remaining portion of the well to add a sample to a reservoir defined by the well.

In yet another aspect, the disclosure relates to a cuvette system that may comprise a disposable cuvette element for holding a sample for analysis. The cuvette element may comprise an elongated strip having an exterior surface with opposite faces, and a well formed on the strip to hold a sample on the strip. The well may include a hole through the strip to hold a defined volume of the sample. The hole may be defined by an edge surface including at least two edge surface portions, with the at least two edge surface portions including at least two edge surface sections including converging and diverging surface sections forming a neck with a gap through which a beam of energy may pass. The cuvette system may also comprise a reusable holder for removably receiving the cuvette element, which may have a substantially hollow interior for receiving at least a portion of the cuvette element. The holder may have a perimeter wall including a front wall and a rear wall of the holder, and a window may be formed in each of the front and rear walls and being generally positioned in alignment with each other. The windows may be alignable with the well in the cuvette element when the cuvette element is inserted into the holder such that a straight line passes through the windows and the well simultaneously.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein:

FIG. 10A is a schematic exploded perspective view of another illustrative embodiment of the strip and holder showing a well formed by converging-diverging edge surface portions.

FIG. 10B is a schematic side sectional view of the embodiment of the strip shown in FIG. 10A.

FIG. 10C is a schematic enlarged side sectional view of a portion of the strip shown in FIG. 10B showing the converging-diverging edge surface portions.

FIGS. 11A through 11K are enlarged side sectional views of various optional configurations of the converging-diverging edge surface portions forming a well in the strip.

FIG. 15A is a schematic exploded perspective view of another illustrative embodiment of the strip and holder showing another configuration of the well having a movable portion.

FIG. 15B is a schematic exploded perspective view of the embodiment of FIG. 15A shown from an opposite perspective.

FIG. 15C is a schematic side sectional view of the strip of FIGS. 15A and 15B.

FIG. 16A is a schematic exploded perspective view of another illustrative embodiment of the strip and holder showing another configuration of the well having a capsule element.

FIG. 16B is a schematic perspective view of the strip and capsule element of the embodiment of FIG. 16A shown in an exploded condition.

FIG. 16C is a schematic side view of the strip of FIG. 16B shown in an assembled condition.

FIG. 16D is a schematic side sectional view of the strip and capsule element of FIG. 16B shown in an exploded condition.

FIG. 17A is a schematic exploded perspective view of another illustrative embodiment of the strip and holder showing another configuration of the well having a capsule element.

FIG. 17B is a schematic side sectional view of the strip and capsule element of the embodiment of FIG. 17A shown in an assembled condition.

FIG. 17C is a schematic side sectional view of the strip and capsule element of the embodiment of FIG. 17A shown in an exploded condition.

FIG. 17D is a schematic side sectional view of an optional configuration of the capsule element of FIG. 17B.

FIG. 18A is a schematic exploded perspective view of another illustrative embodiment of the strip and holder showing another configuration of the well having a capsule element.

FIG. 18B is a schematic exploded perspective view of the embodiment of FIG. 18A shown from an opposite perspective.

FIG. 18C is a schematic side view of the strip of FIG. 18B shown in an assembled condition.

FIG. 18D is a schematic side sectional view of the strip and capsule element of FIG. 18B shown in an exploded condition.

FIG. 19A is a schematic perspective view of an embodiment of the system including an interface portion incorporated with the strip.

FIG. 19B is a schematic side view of the embodiment of the interface portion and strip of FIG. 19A.

FIG. 19C is a schematic front view of the embodiment of the interface portion and strip of FIG. 19A.

FIG. 19D is a schematic front sectional view of the embodiment of the interface portion and strip of FIG. 19A.

FIG. 19E is a schematic side sectional view of the embodiment of the interface portion and strip of FIG. 19A.

FIG. 20A is a schematic front view of the embodiment of the system shown in FIG. 19A in an assembled condition.

FIG. 20B is a schematic front sectional view of the embodiment of the system shown in FIG. 20A.

FIG. 20C is a schematic side sectional view of the embodiment of the system shown in FIG. 20A.

FIG. 21A is a schematic side sectional view of the interface portion shown in FIG. 20C.

FIG. 21B is a schematic top view of the interface portion shown in FIG. 19B with the strips absent.

FIG. 22A is a schematic exploded perspective view of another illustrative embodiment of the system with a modified pipette structure.

FIG. 22B is a schematic partially exploded perspective view of the modified pipette structure of the illustrative embodiment of FIG. 22A.

FIG. 22C is a schematic front sectional view of the modified pipette structure shown in FIG. 22B shown in an assembled condition with the holder.

FIG. 22D is a schematic side sectional view of the modified pipette structure shown in FIG. 22B shown in an assembled condition in the holder.

FIG. 23A is a schematic front view of an illustrative embodiment of the system with the modified pipette structure with a shield inserted into the holder.

FIG. 23B is a schematic front view of an illustrative embodiment of the shield of FIG. 23A.

FIG. 23C is a schematic enlarged perspective view of isolated elements of the modified pipette structure shown in FIG. 22A.

DETAILED DESCRIPTION

Figure 1:
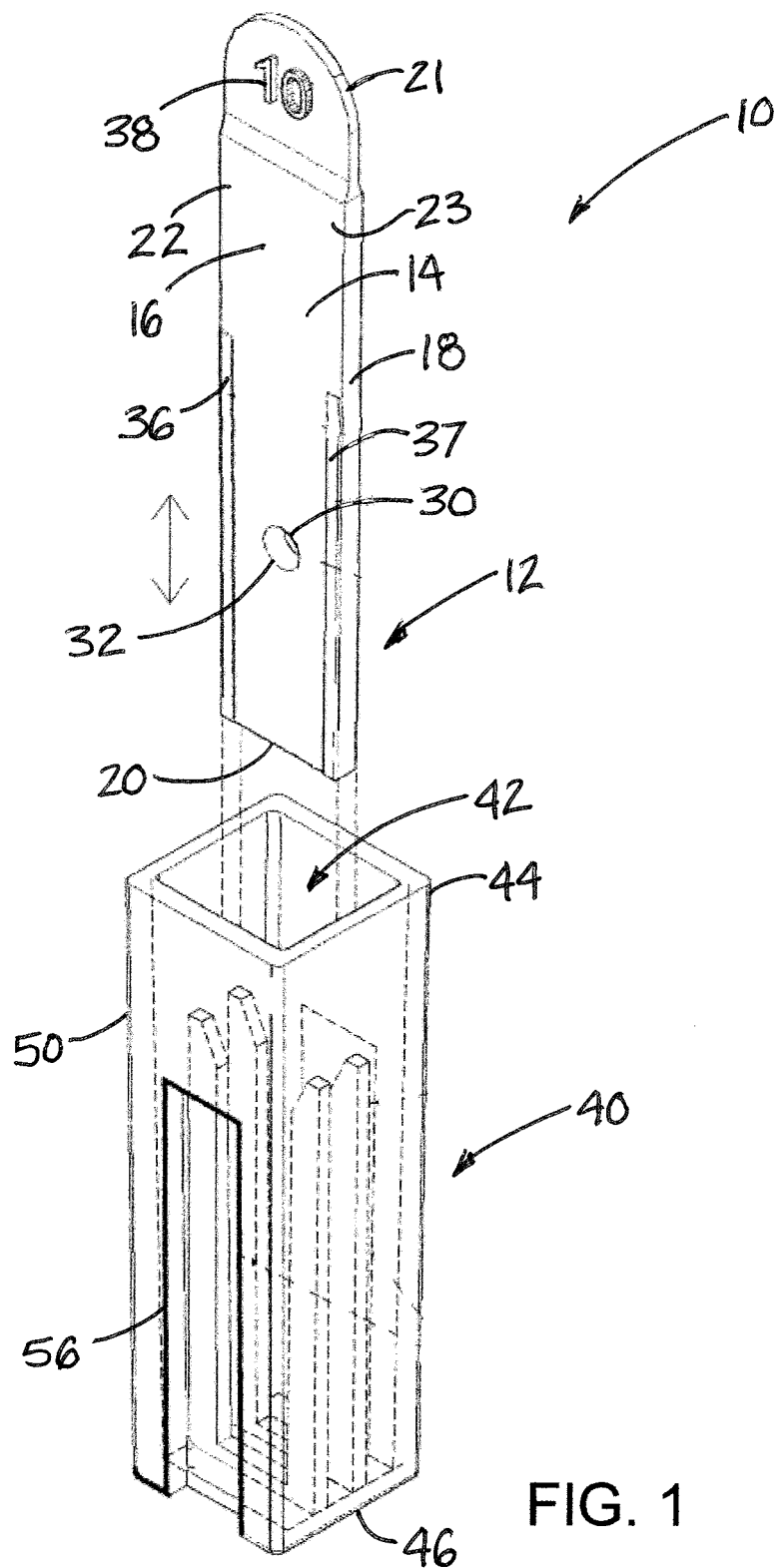
FIG. 1 is a schematic perspective view of a new cuvette system according to the present disclosure in an exploded or disassembled condition.
Figure 2:
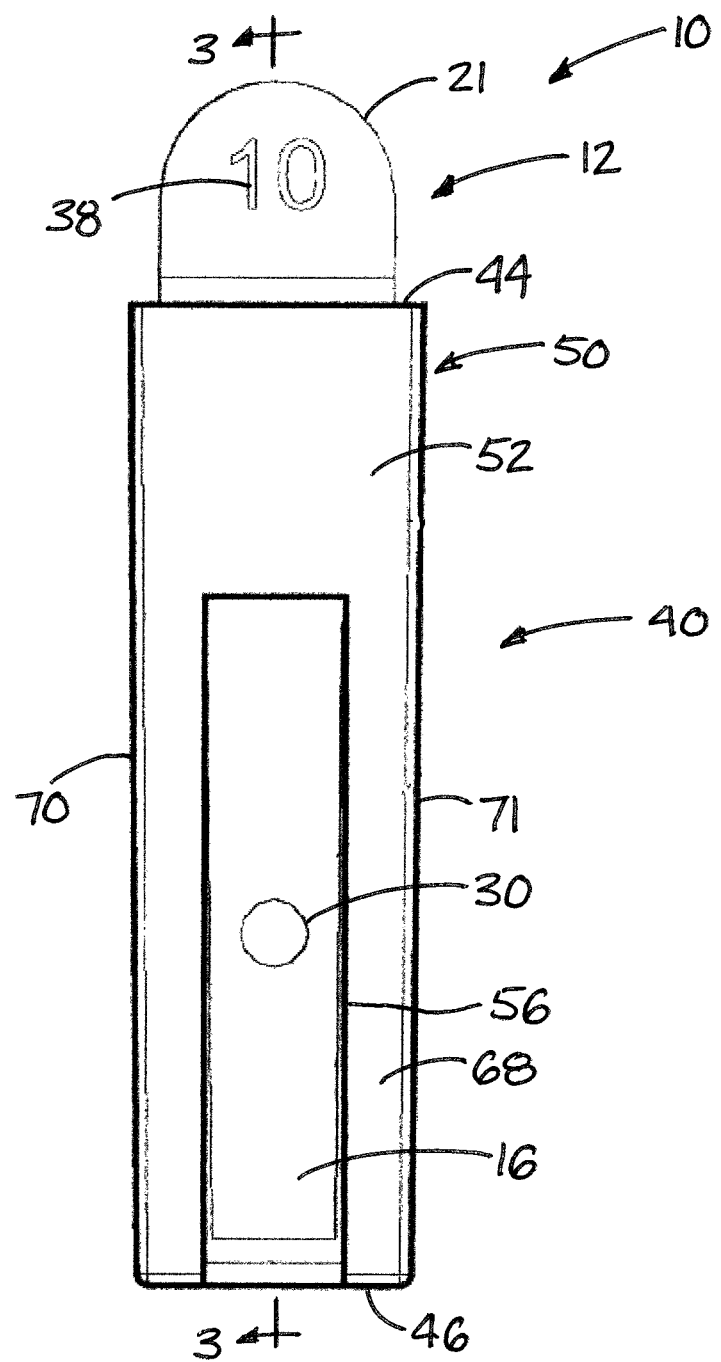
FIG. 2 is a schematic front view of the cuvette system, according to an illustrative embodiment, in an assembled condition.
Figure 3:
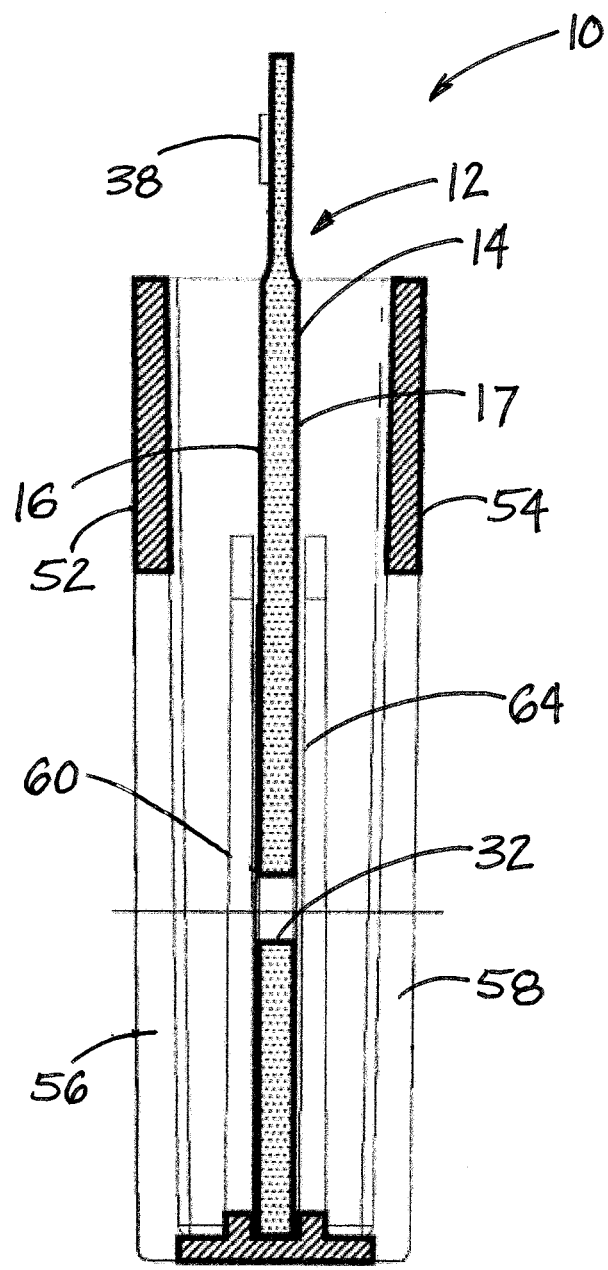
FIG. 3 is a schematic sectional view of the cuvette system, according to an illustrative embodiment, taken along line 3-3 of FIG. 2.
Figures 4A, 4B, 4C, 4D:
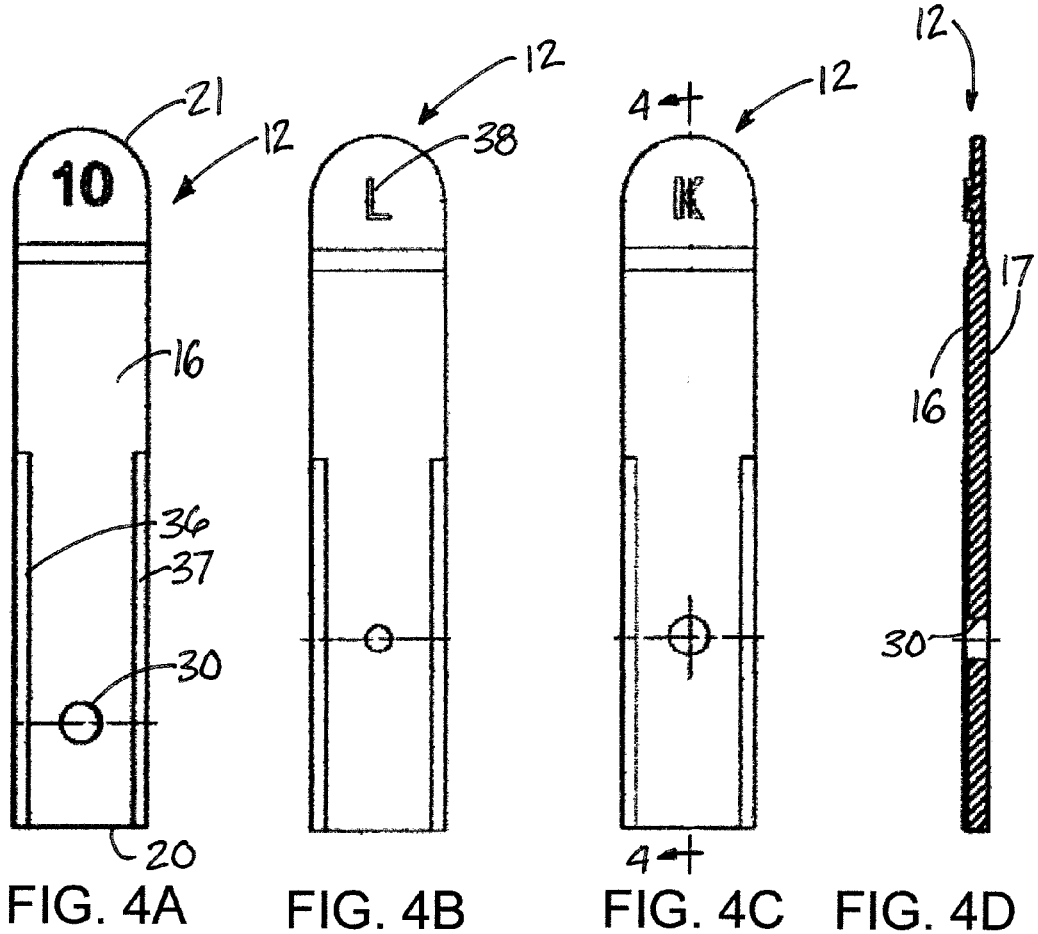
FIG. 4A is a schematic front view of an illustrative embodiment of the cuvette element, with one example of a size and a position of a hole.
FIG. 4B is a schematic front view of another illustrative embodiment of the cuvette element, with another example of a size and a position of a hole.
FIG. 4C is a schematic front view of still another illustrative embodiment of the cuvette element, with still another example of a size and a position of a hole.
FIG. 4D is a schematic section view of the illustrative embodiment of FIG. 4C taken along line 4-4 of FIG. 4C.
Figure 5A:
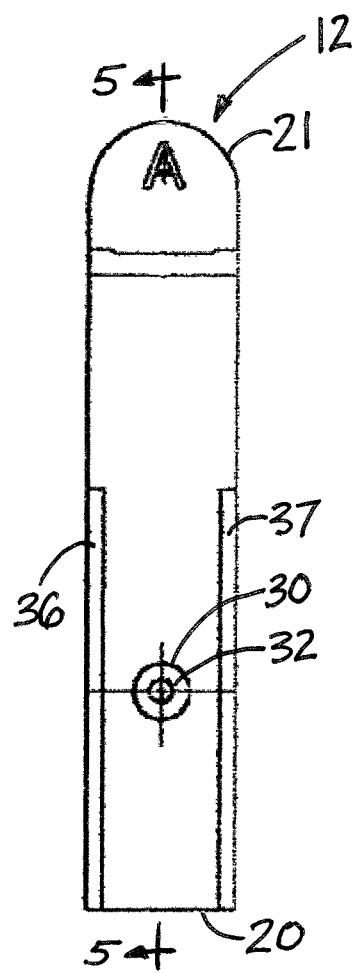
FIG. 5A is a schematic front view of an illustrative embodiment of the cuvette element, with one example of a size and shape of a well.
Figure 5B:
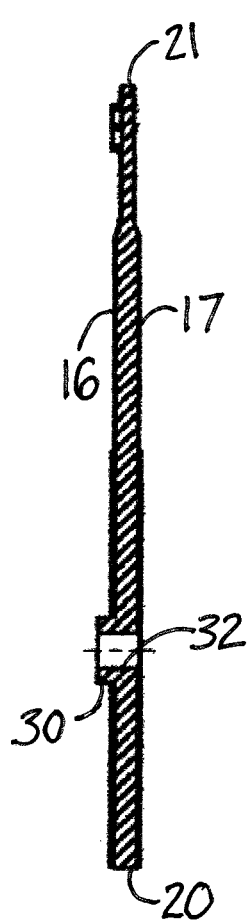
FIG. 5B is a schematic sectional view of an embodiment of the cuvette element, such as the embodiment of FIG. 5A taken along line 5-5 of FIG. 5A.
Figure 5C:
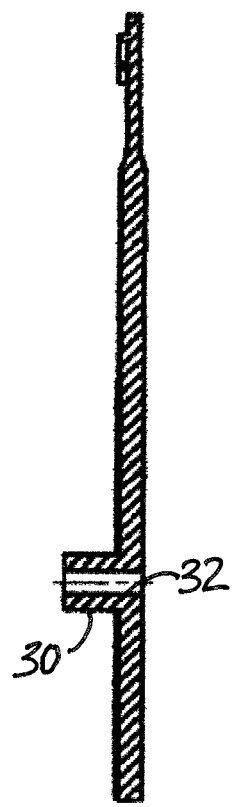
FIG. 5C is a schematic sectional view of an embodiment of the cuvette element, such as the embodiment of FIG. 5A taken along line 5-5 of FIG. 5A.
Figure 6A:
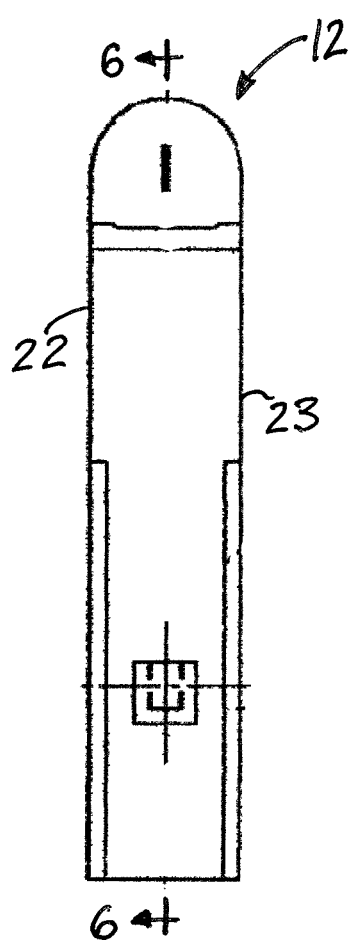
FIG. 6A is a schematic front view of an illustrative embodiment of the cuvette element, with one example of a size and a shape of a well.
Figure 6B:
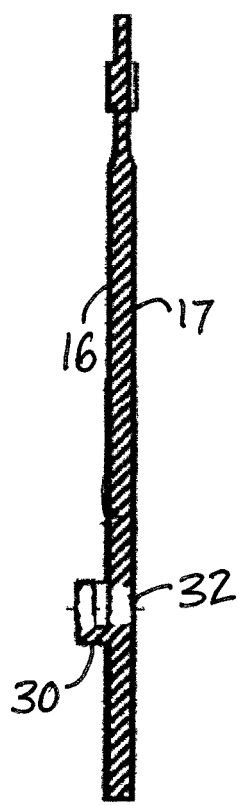
FIG. 6B is a schematic sectional view of an embodiment of the cuvette element, such as the embodiment of FIG. 6A taken along line 6-6 of FIG. 6A.
Figure 6C:
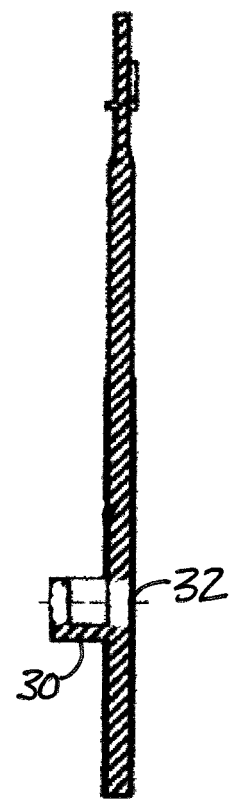
FIG. 6C is a schematic sectional view of an embodiment of the cuvette element, such as the embodiment of FIG. 6A taken along line 6-6 of FIG. 6A.
Figure 7:
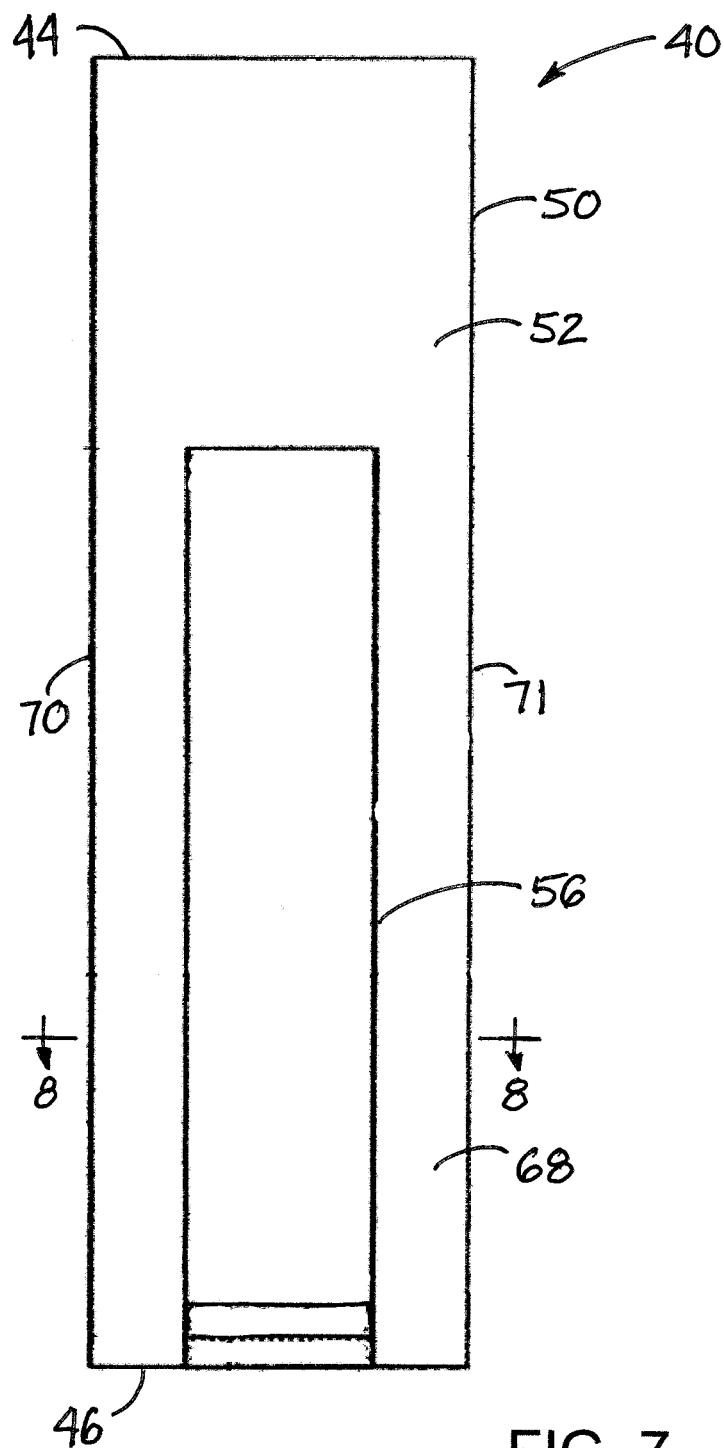
FIG. 7 is a schematic front view of an embodiment of the holder.
Figure 8A:
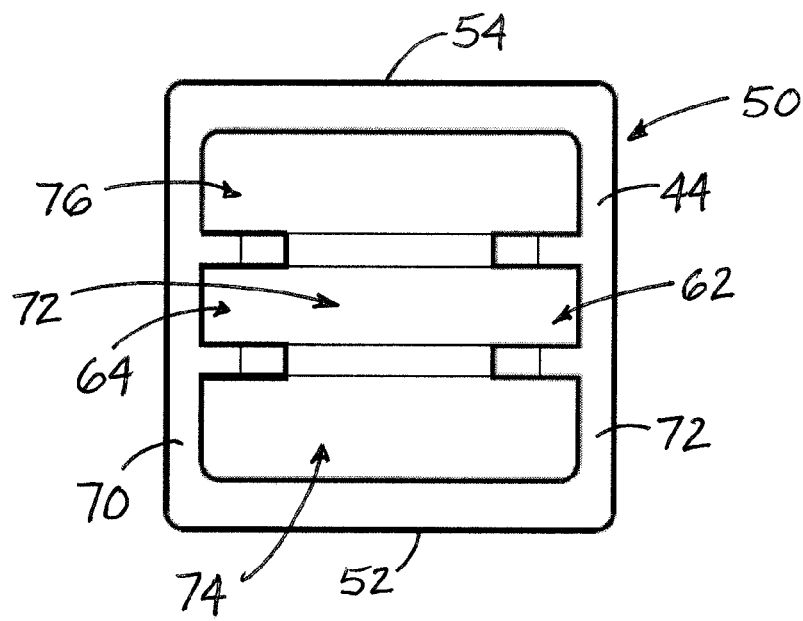
FIG. 8A is a schematic top view of an embodiment of the holder.
Figure 8B:
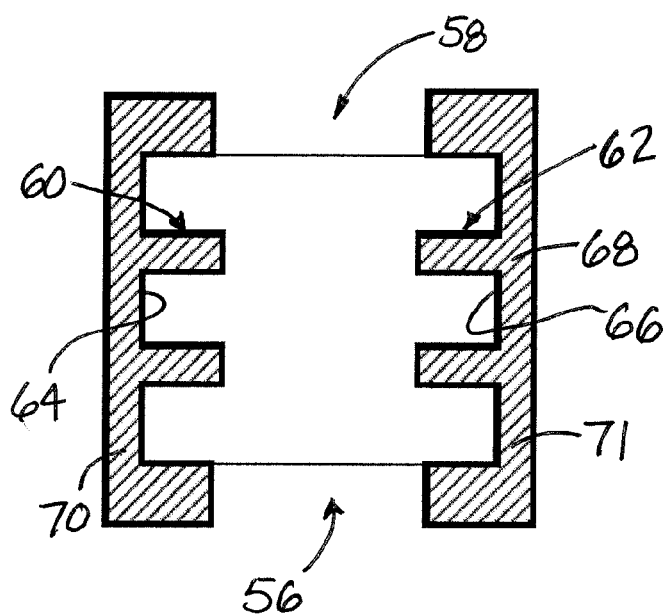
FIG. 8B is a schematic sectional view of an embodiment of the holder taken along line 8-8 of FIG. 7.
Figure 9:
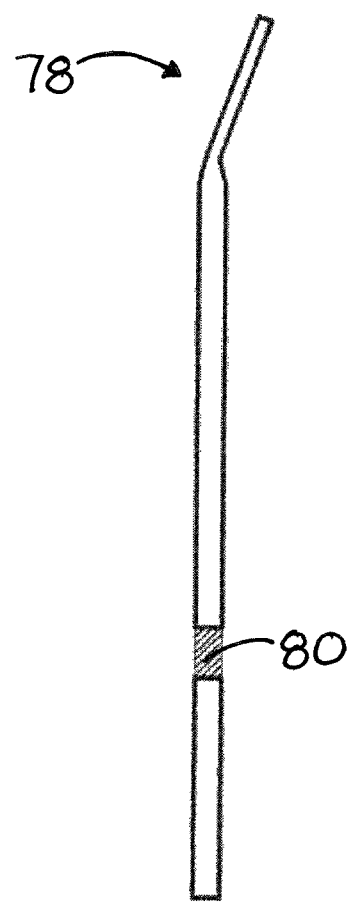
FIG. 9 is a schematic side view of an embodiment of a filter strip.
Figure 12D:
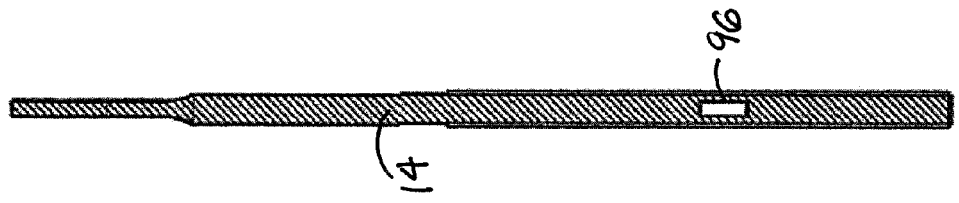
FIG. 12D is a schematic side sectional view of the strip of FIG. 12B showing another one of the passages.
Figure 12C:
FIG. 12C is a schematic side sectional view of the strip of FIG. 12B showing one of the passages.
Figure 12B:
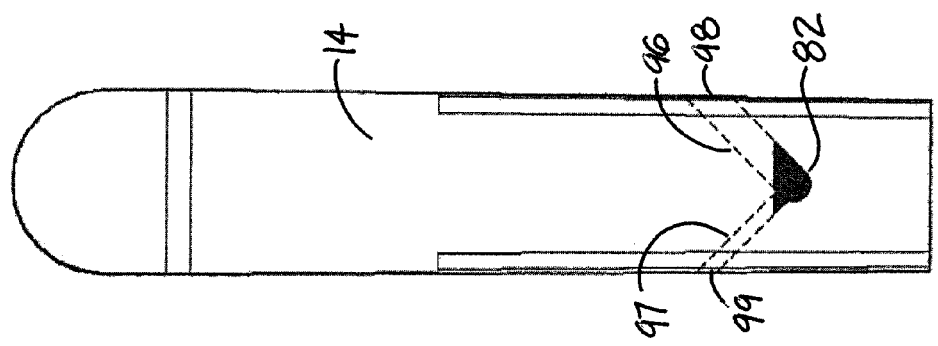
FIG. 12B is a schematic front view of the strip of FIG. 12A showing the well and passages in broken lines.
Figure 12A:
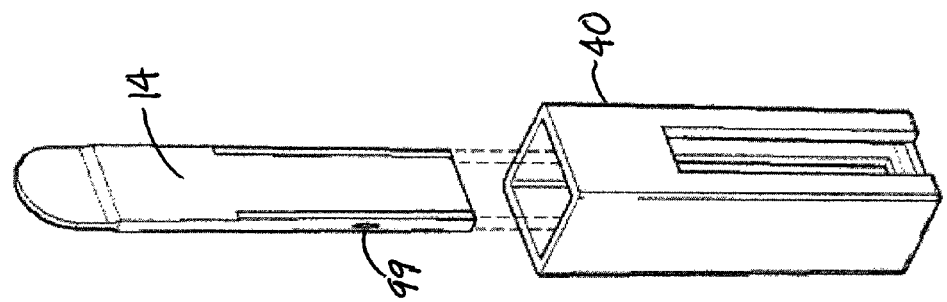
FIG. 12A is a schematic exploded perspective view of another illustrative embodiment of the strip and holder showing a well formed with passages for placing the sample into the well.
Figure 13C:
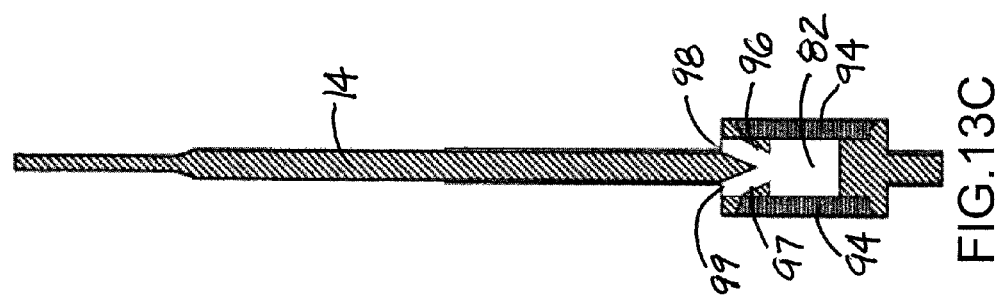
FIG. 13C is a schematic side sectional view of the strip of FIG. 13B.
Figure 13B:
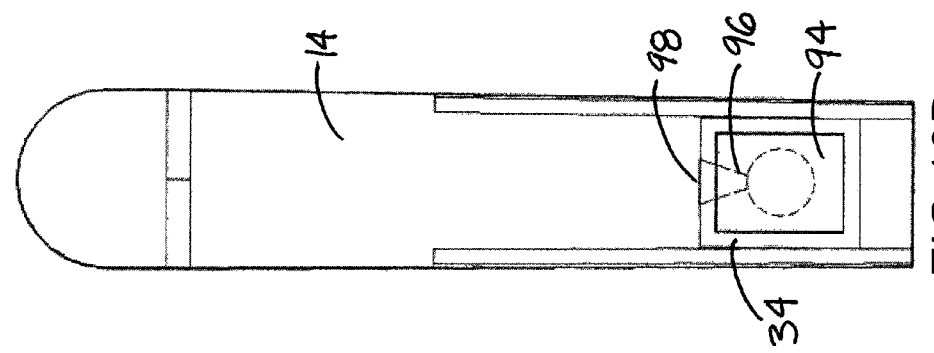
FIG. 13B is a schematic front view of the strip of FIG. 13A.
Figure 13A:
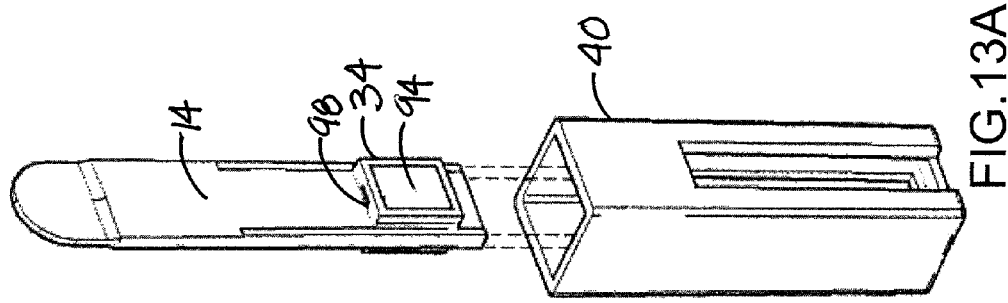
FIG. 13A is a schematic exploded perspective view of another illustrative embodiment of the strip and holder showing another configuration of the well.
Figure 14C:
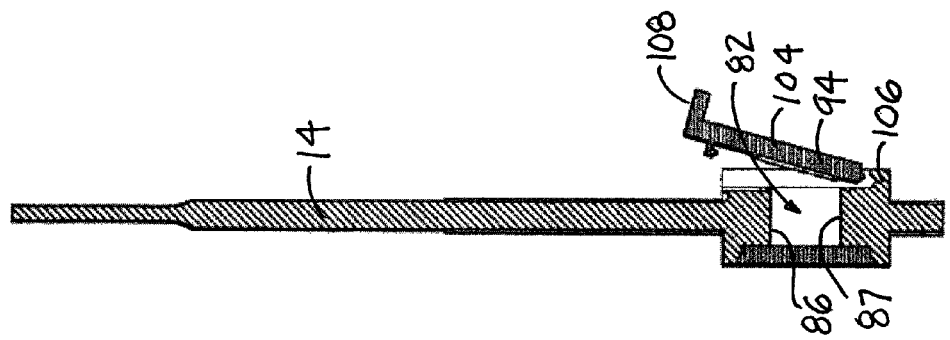
FIG. 14C is a schematic side sectional view of the strip of FIGS. 14A and 14B.
Figure 14B:
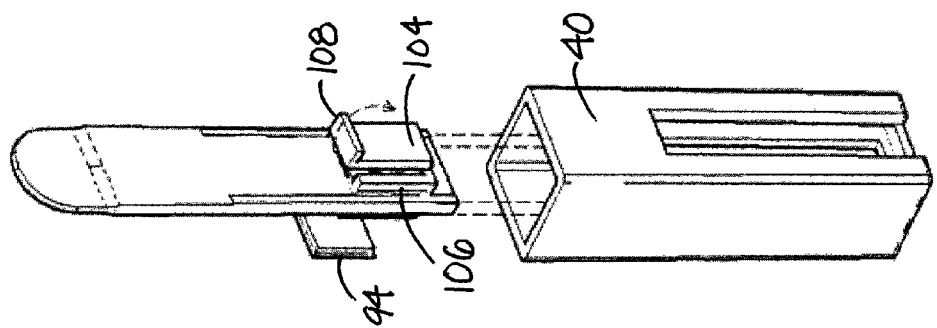
FIG. 14B is a schematic exploded perspective view of the embodiment of FIG. 14A shown from an opposite perspective.
Figure 14A:
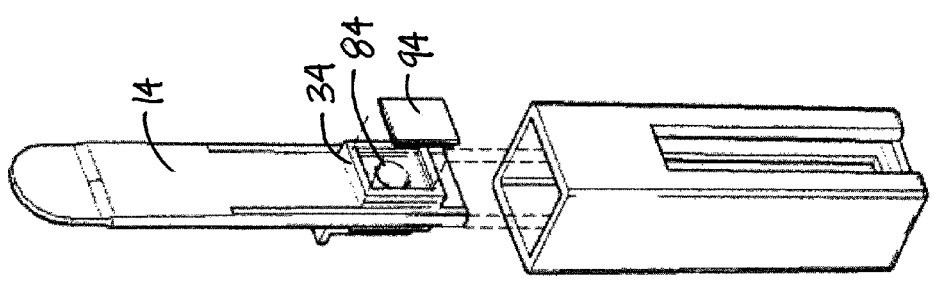
FIG. 14A is a schematic exploded perspective view of another illustrative embodiment of the strip and holder showing another configuration of the well having a movable portion.

With reference now to the drawings, and in particular to FIGS. 1 through 23 thereof, a new cuvette system embodying the principles and concepts of the disclosed subject matter will be described.

Applicant has recognized at least two problems with existing cuvettes. Generally, cuvettes are constructed of relatively expensive materials such that a cuvette must be reused time and time again, or are entirely disposable after a single use. Reusable cuvettes thus require special and vigorous cleaning to avoid contamination between samples use in subsequent tests, and disposable cuvettes are wasteful and may not provide accurate results. Another problem with existing cuvette designs is that the cuvette encloses or encompasses the sample to such a degree that the analyzing beam of the testing equipment must not only pass through the sample but also through a portion of the material forming the cuvette. This factor requires that an adjustment be taken into consideration in analyzing the results produced by the analyzing machine since the beam is not only passed through the sample material but also through the cuvette material which alters or skews the results of the testing.

In view of these problems, the applicant has devised a cuvette system in which only a portion of the cuvette contacts and holds the sample, and this portion may be economically disposed of so that there is no need to reuse the portion of the cuvette exposed to the sample and thus no need to perform the rigorous cleaning of the cuvette. In the new cuvette system, a significant portion of the cuvette system simply acts as a holder for the disposable portion of the cuvette, and may be reused with other sample holding portions. The interchangeability of the applicant's cuvette system also permits an adjustment of the sample holding portion for a particular sample size to be analyzed so that an entire and separate cuvette is not required for each different sample size. Furthermore, and significantly, embodiments of the cuvette system may be configured such that the beam of energy passing through the sample does not have to pass through the material forming the cuvette, and no adjustment to the results of the analysis needs to be made to account for results produced by the cuvette material. This aspect may greatly simplify the analysis needed for use of the cuvette system as adjustments are not necessary for results changed by the material of the cuvette.

In one aspect, the disclosure relates to a cuvette system 10 for generally providing the ability to perform various types of analysis, such as spectrophotometric analysis, on a sample without requiring that the cuvette system 10 be entirely discarded, or that some manner of cleaning be applied to the cuvette system. In general, the cuvette system 10 includes a disposable cuvette element 12 for holding a sample to be analyzed, and a reusable holder 40 for removably receiving a cuvette element in a manner suitable for performing an analysis on the sample. In some of the most preferred embodiments, the cuvette element 12 is disposed after it is used to hold a sample, and the holder 40 may be reused with another cuvette element holding another sample.

In greater detail, the cuvette element 12 may include an elongated strip 14 which may have opposite faces 16, 17, and the distance between the faces may define a thickness therebetween. The strip 14 may have a substantially uniform thickness, although strips of non-uniform thickness may also be utilized. The strip 14 may also have a perimeter edge 18 which may be generally rectangular in shape, although in some embodiments such as the illustrative embodiments, one end of the strip intended to be gripped by the fingers of the user may have a rounded or curved profile. The perimeter edge may include a pair of opposite end edge portions 20, 21 including a lower end edge portion 20 and an upper end edge portion 21, and illustratively the lower end edge portion 20 may be substantially linear and straight while the upper edge end portion may have a semicircular or generally rounded shape. The perimeter edge 18 may also include a pair of opposite side edge portions 22, 23 which illustratively are substantially linear and straight and substantially parallel to each other such that the strip has a substantially uniform width between the end edge portions, although other configurations may be utilized.

The cuvette element 12 may also include a well 30 for receiving the sample to be analyzed and holding the sample on the strip as the cuvette element 12 is moved into and out of the holder 40. The well may be configured with a certain size or volume to hold a defined volume of the sample, and the defined size or volume may varied from one element 12 to another element to permit the system to be easily adapted for use the size of the particular sample to be tested. For example, well sizes such as 1 microliter, 2 microliters, 4 micro liters and 10 microliters may be utilized, but other sizes larger, smaller or in between these sizes may also be used. Of course, it will be recognized that despite a defined volume, the sample positioned by the user in the well may be less than or greater than the defined size. A hole 32 may form at least a portion of the well 30, and may extend through the strip 14, such as between the opposite faces 16, 17. The hole of the well may have an area that is sized for defining a particular volume of the sample to be held therein.

In some embodiments, the well may include a wall 34 that may generally extend around the hole 32 and may extend from at least one of the opposite faces of the strip in order to increase the volume of the sample capable of being held in the well 30. In some embodiments, the wall 34 may be generally cylindrical in shape, while in other embodiments the wall may be generally rectangular. With some implementations the rectangular wall may have an open upper side. In the most preferred embodiments, the well provides a space for receiving a sample that is not obstructed by the material forming the well at least along an axis extending perpendicular to the plane of the faces of the elongated strip 14. This permits a beam of light or energy or particles from an analysis machine to pass directly through the sample without also passing through a portion of the cuvette element 12. Further, the position of the well 30 with respect to the strip 14, and more particularly with respect to the lower end edge portion 20, may vary from one strip to another to accommodate the physical configuration of various analysis machines.

In some embodiments of the cuvette element 12, at least one rail 36 may be formed on at least one of the opposite faces of the elongated strip 14, and may protrude from the face for a distance. Some embodiments may include a pair of rails 36, 37 that protrude from the same face of the strip 14 in order to provide a relatively thicker edge thickness relative to the thickness of the majority of the strip. The rails 36, 37 may be substantially linear, and may be formed on one or both faces of the strip. Each of the rails may be positioned along at least a section of one of the side edge portions of the perimeter edge of the strip. In addition to providing a relatively thicker thickness for the cuvette element 12 along the side edge portions of the strip 14, the rails may also provide a degree of resistance to bending of the strip by imparting additional rigidity.

The cuvette element 12 may also include a marking 38 positioned on the strip which provides information to the user including a relative size or capacity of the well directly in a volume measurement or symbolically through the user of letters or numbers or other indicia.

The reusable holder 40 of the cuvette system 10 may be configured for removably receiving a cuvette element 12, and may be intended to be used with a plurality of interchangeable and replaceable elements 12 such that the cuvette element 12 may be disposed of after a single use while the holder 40 continues to be used for many uses with additional cuvette elements. Additionally, the interchangeability of the cuvette element in the holder 40 permits the holder to be used with a variety of different cuvette elements having different sample capacities (and not only a single capacity). The holder 40 may have a substantially hollow interior 42 for receiving at least a portion of the cuvette element (and not necessarily the entire element 12, although that option may be utilized). The holder may be sized such that an upper portion of the cuvette element remains outside of the interior when the element 12 is fully inserted into the holder to provide a finger-gripping location on the element 12 that remains accessible to the user's fingers for removal after use.

The holder 40 may have an open top end 44 and may also have a substantially closed bottom end 46. The holder may also have a perimeter wall 50 generally extending between the top end 44 and bottom end 46. The perimeter wall may include a front wall 52 and a rear wall 54 which are positioned generally in opposition to each other with respect to the perimeter wall, and may also include opposite sidewalls 70, 71 which extend between the front and rear walls.

Windows 56, 58 may be formed in opposite walls of the holder, such as the front and rear walls. Illustratively, the window 56 may be formed in the front wall 52 and the window 58 may be formed in the rear wall 54. The windows 56, 58 may be generally positioned in alignment with each other, while exact registration and coextension of the windows is not required. The windows 56, 58 may be configured to be aligned with the well 30 in the cuvette element 12 when the cuvette element is inserted into the holder such that a beam of energy passing through the well 30 also passes through the windows 56, 58 so that the beam of energy does not pass through material of the cuvette element 12 or the holder 40 when the cuvette element is inserted into the holder. Thus, a straight line may be able to pass though the well 30 and the windows 56, 58 simultaneously when the element 12 is inserted into the holder 40.

The holder 40 may include at least one guide 60 that is formed in the interior of the holder, and in at least some embodiments the guide 60 includes opposing sets of guides 60, 62 that define opposing channels 64, 66 that are configured and positioned to receive the opposite side edge portions of the strip 14 of the cuvette element when the element is inserted into the interior of the holder for use. The guides 60, 62 may be formed on the interior surfaces of the side walls 70, 71 such that the strip 14 is positioned between the windows 56, 58. The channels 64, 66 may be configured to hold the cuvette element 12 in a position that is spaced from the front and the rear walls of the holder. In at least some embodiments, the exterior surface 68 of the holder has a cuboid shape with sides of generally rectangular shape, but may be configured for use in the space provided in an analysis machine for conventional cuvettes.

In some embodiments, the guides 60, 62 and channel form a central position 72 in the interior 42 of the holder, and may also form a front position 74 between the guides and the front wall 52 of the perimeter wall. The guides may also form a rear position 76 between the guides and the rear wall 54 of the perimeter wall. The front and rear positions may be suitable for receiving a strip 14 of the type suitable for holding a sample, but in some embodiments a filter strip 78 may be positioned in one or the other of the front and rear positions in conjunction with a strip 14 in the central position. The filter strip 78 (see FIG. 9) may function to filter the beam entering the sample in the strip 14, or filter the beam leaving the sample. For example, a filter strip 78 positioned in the front position 74 may encounter the beam first and perform excitation filtering on the beam before the beam passes through the sample. As another example, a filter strip 78 positioned in the rear position 76 may encounter the beam after the beam has passed through the sample, and perform emission filtering on the beam after the beam passes through the sample. Illustratively, the filter strip 78 may be similar to the strip 14 with a window 80 of filtering material that is alignable with the well of the strip 14 when the strip is inserted into the central position. The filtering material may be selected for filtering the desired wavelength or wavelengths of energy. The strip 78 may have a bent upper tab portion that may facilitate the finger gripping of the tab portion when a strip 14 is located in the central position of the holder.

In use of the cuvette system 10, a holder 40 may be obtained and a suitable cuvette element 12 may be selected based upon, for example, the size of the sample available or the desired size of the sample to be tested. The user may select a cuvette element 12 from a plurality of cuvette elements having differently-sized wells 30, with the user selecting the cuvette element with a well that is suitably sized for the particular size of the sample to be tested. The sample material may be positioned in the well of the selected cuvette element, and the cuvette element may be inserted into the holder interior through the open top end 44 of the holder, preferably with the lower end portion of the cuvette element being inserted first into the interior. The cuvette element may be inserted into the holder at least until the well 30 is positioned between the windows 56, 58 of the holder. When the cuvette element 12 is fully inserted into the holder 40, a portion of the element 12 may protrude from the top end 44 of the holder to provide a location on the element 12 for the user to grip the element 12 with his or her fingers in order to be able to remove the element 12 from the holder after testing. The assembled holder and element may be inserted into the testing apparatus, and the test may be conducted. After the testing has been concluded, the cuvette system 10 may be removed from the analysis machine and the cuvette element 12 may be removed from the holder and element 12 may be discarded in a suitable manner while the holder 40 may be retained for future use with another cuvette element 12 as well as a different sample.

The applicant has also recognized that when attempting to apply a beam of energy to measure the spectrum, absorbance or transmission wave length of a sample of a relatively small volume, such as approximately 2 micro liters or less, or approximately 0.5 to approximately 1 micro liters, evaporation of at least a portion of the sample can be a significant problem, especially if the solvent of the sample is a volatile substance. Evaporation of the solvent from the sample tends to concentrate the sample and distort the accuracy of measurements such that accurate repeatable measurements are not usually possible unless the operator tightly controls the environment in which the measurements are made, including the temperature of the environment in which the measurements are made as well as the time between obtaining the sample and measuring the sample, Higher temperatures and longer delays between obtaining the sample and analyzing the sample tend to encourage evaporation and concentrate the sample, thus distorting the measurements obtained from the sample.

The applicant has developed embodiments of the cuvette system that reduces and minimizes if not eliminates the opportunity for portions of the sample to evaporate in the time that may be required to take a measurement using the sample. Embodiments are designed to minimize the exposure of the sample to environmental air to minimize the opportunity for the sample, or solvent in the sample, to evaporate into the air and thus concentrate the remainder of the sample. Illustratively, some embodiments employ a port or ports for loading the sample into the well with the ports that greatly reducing the ability of air to reach the sample. Some embodiments may allow the sample to be sealed in the well after adding the sample to the well or reservoir, such as by, for example, panels or shutters or the like.

Advantageously, stability of the sample is enhanced and permits longer preparation time without fear of concentrating or losing the sample. For example, multiple samples can be prepared before analysis begins rather than having to test each sample after preparation for fear of losing a portion of the sample to the air and distorting the result. Further, samples can be transported over a distance, such as from one lab to another lab or from the field to a lab in a reasonable time period without concern of significant changes in the concentrations of a sample. Further, greater isolation of the samples from the environment may increase the safe handling of the samples, and decrease the opportunity to contaminate the environment or the operator, as well as minimizing the potential for contaminating the sample. Typically, the well may be configured to hold samples with relatively smaller volumes such as, for example, approximately 1 to approximately 10 micro liters of sample in a closed environment. This range is believed to be much smaller than conventional micro cuvettes which typically hold 50 to 70 to 50 micro liters. Systems that are available for holding samples in the ultra micro range (0.5 to 1 micro liter) are typically not disposable, are expensive and are an open system subject to the problems explained above.

As illustratively shown in FIGS. 10 and 11, at least a portion of the elongated strip 14 and the well 30 may be opaque to the beam of energy. In some embodiments, the entire strip 14 and the well are opaque to the beam of energy, so that only the hole 32 of the well is transparent to the beam of energy.

As also illustratively shown in FIGS. 10 and 11, the hole 32 of the well 30 may define a reservoir 82 for holding the sample. The reservoir 82 may be defined by at least one edge surface 84 of the strip which bounds the reservoir. The edge surface 84 may be circular on a plane that is parallel to one of the faces 16, 17 of the strip 14. The edge surface 84 may form a pair of opposed edge surface portions 86, 87 and the surface portions may extend toward each other while maintaining a gap 88. The edge surface portions may include at least one converging surface section 90 and at least one diverging surface section 91. The width of the gap 88 may thus vary through the thickness of the strip between the faces 16, 17 with a neck 92 of the most limited width being located in the hole at a location at one of the faces or between the faces. For example, FIGS. 11A through 11F show configurations in which the neck is located at one of the faces 16, 17, while in FIGS. 11G through 11K the neck is located between the faces. The edge surface portions may be planar, or may be arcuate with a concave or convex shape. Further, the degree of convergence of the edge surface portions may be relatively slight (e.g., see FIG. 10C) or substantial (see, e.g., FIGS. 11G and 11H).

In some embodiments, the well 30 may be closed on both of the faces 16, 17 of the strip 14 which may be highly advantageous when the size of the sample to be tested is relatively small in size or quantity and possibly subject to the effects of evaporation of a portion of the sample. A windowpane 94 may be formed on each face or may be otherwise mounted on each face of the strip. The windowpane or windowpanes may be positioned in transverse alignment with each other and the hole 32 of the well such that a beam of energy passing through the hole also passes through the windowpane or windowpanes. The material forming the windowpane 94 may be substantially transparent to the beam of energy, particularly if the remainder of the strip is opaque to the beam.

To facilitate movement of the sample into a well in which the face sides of the well are closed, such as by windowpanes, at least one passage 96 may be provided which is in fluid communication with the well 30. The at least one passage 96 may be formed on the strip 14 such as is shown in FIG. 12. The passage may also be in fluid communication with the exterior surface of the strip, and in some embodiments the passage may have a substantially uniform width. The passage 96 may have an opening 98 located opposite of the well and the opening may be located on one of the surfaces of the strip.

Advantageously, the strip may be provided with a first passage 96 and a second passage 97, with the first passage having a first opening 98 in the surface of the strip and the second passage 102 having a corresponding second opening 99 in the strip. The first passage 96 may be utilized to place the sample into the well, and may have a relatively wider width while the second passage 102 may be utilized to vent to air or gas in the well space displaced by the movement of the sample into the well, and may have a relatively narrower width. It should be recognized that it is advantageous to minimize the width of the passages to minimize evaporation through the passages. The opening 98 of the passage may be located on one of the opposite side edge portions 22, 23. The opening 98 of the passage may be located relatively closer to the upper end edge portion 21 of the strip and the well 30 may be located relatively closer to the lower end edge portion 20 of the strip. The first opening of the first passage may be located in a first front edge portion 22 of the strip and the second opening 102 may be located in a second side edge 23 of the strip. Advantageously, the positioning of the openings on the side edges permits the openings to be effectively closed by the channels 64, 66 of the holder when the strip is slid into the holder interior 42. In some embodiments, the opening of the passage may be located on one of the opposite faces 16, 17 of the elongated strip, and the first opening of the first passage may be located in the first face 16 of the strip, and the second opening of the second passage may be located in the second face 17 of the strip.

In some embodiments, at least a portion of the well 30 may be movable with respect to the elongated strip 14, such as shown in the illustrative embodiments of FIGS. 13 through 18, and the movable portion may include at least one of the windowpanes 94. The well may thus include a movable portion 104 which may be pivotable with respect to remaining portions 106 of the well (see, e.g., FIGS. 13 through 15). The movable portion 104 may be removable from the remaining portions 106 (see, e.g., FIGS. 16 through 18), and in some embodiments the movable portion may be slidable with respect to the remaining portions. Optionally, the movable portion may include a handle tab 108 which is formed on the movable portion to permit gripping of the handle and movement of the movable portion by the fingers of the user.

The movable (or removable) portion 104 may include a capsule element 110 which may be movable into a space 112 defined by the remaining portions of the well. The capsule element 110 may define a capsule interior 114 for receiving the sample to be tested, and the capsule element may be movable out of one or both of the faces 16, 17 of the strip. The removable capsule element 110 may include at least one of the windowpanes 94, and may include both of the windowpanes. The capsule element 110 may have an open top 116 which may be closed by the remaining portions 106 of the well when the movable portion is moved into the space 112. Illustratively the capsule may have a cubic shape (see, e.g., FIG. 16) or a cylindrical shape (see, e.g., FIG. 17) in shape, although other shapes may be employed. The capsule element may 110 have side walls 118, 119 and a bottom wall 120, and may be slidable into the space 112. Optionally, the capsule element may have engagement nubs 122 (see, e.g., FIGS. 16 and 17) to position the capsule element in the space, and may be configured to releasably hold the capsule element in the space such that the capsule is removable to position a sample in the capsule interior 114 but may also be held in the space during analysis of the sample. In some embodiments, the removable capsule 110 may include a removable cap 124 (see, e.g., FIG. 17) which may incorporate one of the windowpanes. The removable cap may form a stop 126 for restricting movement of the capsule element with respect to the strip 14.

In some embodiments, the removable capsule element 110 may have one passage 96 formed therein (see, e.g., FIG. 18) or two passages 96, 98 formed therein (see, e.g., FIG. 13), and the passage or passages may be in fluid communication with the capsule interior 114. The opening 98 of the passage 96 may be selectively closed when the capsule element is inserted into the well (see, e.g., FIG. 18), and a rim 128 extending about the space defined by the well may be configured to block the opening 98 of the passage when the capsule element is inserted into the well.

In some embodiments, the cuvette element 12 may include an interface portion 130 for interfacing or connecting the strip to a pipette to facilitate transfer of a sample from a pipette to the well of the strip. The interface portion 130 may extend from the elongated strip element 14, and may be integral with the strip. The interface portion 130 may have an upper end 132 and a lower end 133. The interface portion 130 may have an upper aperture 134 located at the upper end 132 and a lower aperture 136 located at the lower end 133. The interface portion may be in fluid communication with the reservoir 82 of the well through the lower aperture. The interface portion may extend from the upper end edge portion 21 of the strip and may bisect the upper end edge portion. The interface portion 130 may be configured to extend out of the open top end 44 of the holder 40 when the strip is inserted into the interior of the holder. The interface portion 130 may have a cavity 138 configured to receive a portion of a pipette, and the cavity may extend from the upper end 132 to the lower end 133. The cavity 138 may have a width, and the width may taper smaller toward the lower end 133 of the interface portion to resemble the profile of the outer surface of a pipette. The wall 34 of the well 30 may be mounted on the lower end 133 of the interface portion, and may extend laterally from the lower end 133. In some embodiments, the wall 34 may extend in opposite directions from the strip and may be tubular. Illustratively, the tubular wall 34 may be substantially cylindrical with an interior diameter, and the interior diameter may be relatively larger toward a first end 140 of the wall and the interior diameter may be relatively smaller toward a second end 142 of the wall. Optionally, the length of the wall between the first and second ends may be substantially equal to the distance between the front 52 and rear 54 walls of the perimeter wall of the holder to help locate the strip in the holder.

In further embodiments, such as is shown in FIGS. 22 and 23, features of a pipette, the interface portion and the strip may integrated together so that the same element, a modified pipette structure 144, may be utilized to pick up a sample and support the sample in the holder 40 of the cuvette system, and can simplify the process of collecting and testing a sample. The modified pipette structure 144 may include alignment rails 145 that engage the channels on the holder, and may include a tip portion 146 used to suction the sample into the interior of the structure 144, such as into a reservoir 148 in the structure, and openings may be formed in the outer wall of the pipette structure that align with the reservoir and through which the beam of energy may pass during analysis. The modified pipette structure 144 may also include a filter or filters 150, 151 positioned above and/or below the reservoir 148 to block portions of the beam of energy that might otherwise travel through the apparatus above or below the sample located in the reservoir, and the filters may thus be located in the pipette structure above and below the reservoir. The reservoir may be defined by surfaces that converge and diverge and may form a neck.

Optionally, a shield 152 that is opaque to the energy of the beam and is separate from the modified pipette structure may be insertable into the holder 40 so that the shield obstructs at least a portion of the window in the holder. The shield may have a substantially U-shaped configuration (see, e.g., FIG. 23B, with the base of the U-shape providing a major portion of the energy blockage (see, e.g., FIG. 23B).

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps described and shown in the disclosure may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A cuvette system comprising:
a disposable cuvette element for holding a sample for analysis, the cuvette element comprising an elongated strip having an exterior surface with opposite faces, and a well formed on the strip to hold a sample on the strip, the well defining and maintaining a closed space forming a reservoir configured to hold a defined volume of the sample to be held in the strip, at least one passage being formed in and extending through the strip between the well and an opening in the exterior surface of the strip such that the passage is in fluid communication with the reservoir and with the opening; and
a reusable holder for removably receiving the cuvette element, the holder having a substantially hollow interior for receiving at least a portion of the cuvette element, the holder having a perimeter wall including a front wall and a rear wall of the holder, a window being formed in each of the front and rear walls and being generally positioned in alignment with each other, the windows being alignable with the well in the cuvette element when the cuvette element is inserted into the holder such that a straight line passes through the windows and the well simultaneously.

2. The system of claim 1 wherein the at least one passage comprises a first passage and a second passage, each of the passages being in communication with the reservoir and having a separate said opening in the exterior surface of the strip.

3. The system of claim 2 wherein the openings of the first passage and the second passage are located on opposite side edges of the exterior surface of the strip.

4. The system of claim 1 wherein the opening of the at least one passage is located relatively closer to an upper end edge of the strip and the well is located relatively closer to a lower end edge of the strip.

5. A cuvette system comprising:
a disposable cuvette element for holding a sample for analysis, the cuvette element comprising an elongated strip having an exterior surface with opposite faces, and a well formed on the strip to hold a sample on the strip, the well defining a closed space forming a reservoir configured to hold a defined volume of the sample to be held in the strip; and
a reusable holder for removably receiving the cuvette element, the holder having a substantially hollow interior for receiving at least a portion of the cuvette element, the holder having a perimeter wall including a front wall and a rear wall of the holder, a window being formed in each of the front and rear walls and being generally positioned in alignment with each other, the windows being alignable with the well in the cuvette element when the cuvette element is inserted into the holder such that a straight line passes through the windows and the well simultaneously;
wherein the well of the strip includes a movable portion and a remaining portion, the movable portion being movable with respect to a remaining portion of the well to add a sample to a reservoir defined by the well; and
wherein the movable portion of the well includes a capsule element defining a capsule interior to form the reservoir, the capsule element being movable into a space defined by the remaining portion of the well and being removable from the space defined by the remaining portions of the well.

6. The system of claim 5 wherein the reservoir is defined by a hole formed through the strip and bounded on each side by a windowpane.

7. The system of claim 5 wherein the movable portion includes at least one windowpane.

8. The system of claim 5 wherein the movable portion of the well is pivotable with respect to the remaining portion of the well.

9. A cuvette system comprising:
a disposable cuvette element for holding a sample for analysis, the cuvette element comprising an elongated strip having an exterior surface with opposite faces, and a well formed on the strip to hold a sample on the strip, the well including a hole through the strip to hold a defined volume of the sample, the hole being defined by an edge surface including at least two edge surface portions, the at least two edge surface portions including at least two edge surface sections including converging and diverging surface sections forming a neck with a gap through which a beam of energy may pass; and a reusable holder for removably receiving the cuvette element, the holder having a substantially hollow interior for receiving at least a portion of the cuvette element, the holder having a perimeter wall including a front wall and a rear wall of the holder, a window being formed in each of the front and rear walls and being generally positioned in alignment with each other, the windows being alignable with the well in the cuvette element when the cuvette element is inserted into the holder such that a straight line passes through the windows and the well simultaneously.

10. The system of claim 9 wherein a windowpane is positioned on opposite sides of the hole adjacent to the opposite faces of the strip to form a reservoir for receiving a sample.

11. The system of claim 9 wherein the edge surface is substantially circular in a plane parallel to one of the faces of the strip.

12. The system of claim 9 wherein the edge surface sections converge toward one of the faces of the strip.

13. The system of claim 9 wherein the edge surface sections converge toward each of the faces of the strip.

14. The system of claim 9 wherein the edge surface sections diverge away from one of the faces of the strip.

15. The system of claim 9 wherein the edge surface sections diverge away from each of the faces of the strip.

16. The system of claim 9 wherein at least one of the edge surface sections is planar.

17. The system of claim 9 wherein at least one of the edge surface sections is concave.

18. The system of claim 9 wherein at least one of the edge surface sections is convex.

19. The system of claim 9 wherein the hole has an opening in each of the opposite faces of the strip, and wherein a width of a first one of the openings is larger than a width of a second one of the openings.

* * * * *